(12) United States Patent
Sagawa

(10) Patent No.: US 12,706,217 B2
(45) Date of Patent: Aug. 11, 2026

(54) AI IMAGE DIAGNOSIS DEVICE AND DENTAL OCT IMAGE DIAGNOSIS DEVICE

(71) Applicant: THE YOSHIDA DENTAL MFG. CO., LTD., Tokyo (JP)

(72) Inventor: Takanobu Sagawa, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 41 days.

(21) Appl. No.: 18/730,360

(22) PCT Filed: Dec. 1, 2022

(86) PCT No.: PCT/JP2022/044362
§ 371 (c)(1),
(2) Date: Jul. 19, 2024

(87) PCT Pub. No.: WO2023/145254
PCT Pub. Date: Aug. 3, 2023

(65) Prior Publication Data

US 2025/0118433 A1 Apr. 10, 2025

(30) Foreign Application Priority Data

Jan. 28, 2022 (JP) ................................ 2022-011470

(51) Int. Cl.
*G16H 50/20* (2018.01)
*A61C 19/04* (2006.01)
*G06T 7/00* (2017.01)

(52) U.S. Cl.
CPC ............. *G16H 50/20* (2018.01); *A61C 19/04* (2013.01); *G06T 7/0012* (2013.01); (Continued)

(58) Field of Classification Search
CPC .................. G16H 50/20; G06T 7/0012; G06T 2207/10072; G06T 2207/20081
See application file for complete search history.

(56) References Cited

U.S. PATENT DOCUMENTS

2014/0192323 A1 7/2014 Kakuma
2018/0146857 A1* 5/2018 González Fernández .................. A61B 5/0075

(Continued)

FOREIGN PATENT DOCUMENTS

EP 1207495 A1 5/2002
JP 2012100825 A 5/2012

(Continued)

OTHER PUBLICATIONS

International Search Report & Written Opinion pertaining to PCT/JP2022/044362, mailed Feb. 14, 2023.

(Continued)

*Primary Examiner* — Reginald R Reyes
(74) *Attorney, Agent, or Firm* — GRUMBLES LAW PLLC; Brittany Haanan

(57) ABSTRACT

An AI image diagnosis apparatus into which three-dimensional tooth image data captured by a dental OCT device is inputted and which analyzes the inputted three-dimensional tooth image data, comprising: a model executor that sequentially inputs two-dimensional tomographic image data constituting the diagnostic target three-dimensional tooth image data into a trained model, to thereby obtain, as an execution processing result of the trained model, lesion information data, which is data related to a part identified as a characteristic part such as a lesion in the inputted tomographic image data, for each piece of tomographic image data in the three-dimensional tooth image data, and detect lesions from the inputted three-dimensional tooth image data using the obtained lesion information data, wherein the trained model is constructed by training of three-dimensional tooth image data of multiple examinees captured by a dental OCT device in the past.

14 Claims, 16 Drawing Sheets

(52) U.S. Cl.
CPC ............... *G06T 2207/10072* (2013.01); *G06T 2207/20081* (2013.01); *G06T 2207/30036* (2013.01)

(56) References Cited

U.S. PATENT DOCUMENTS

| | | | | |
|---|---|---|---|---|
| 2018/0310825 | A1 | 11/2018 | Kakuma et al. | |
| 2021/0074425 | A1* | 3/2021 | Carter | G16H 30/40 |
| 2021/0127969 | A1 | 5/2021 | Oggenfuss et al. | |
| 2022/0386864 | A1 | 12/2022 | Higuchi | |

FOREIGN PATENT DOCUMENTS

| | | | |
|---|---|---|---|
| JP | 2012100826 | A | 5/2012 |
| JP | 2012213433 | A | 11/2012 |

OTHER PUBLICATIONS

Office Action pertaining to Indian Patent Application No. 202417056920, mailed Mar. 26, 2026.

* cited by examiner

FIG. 7A
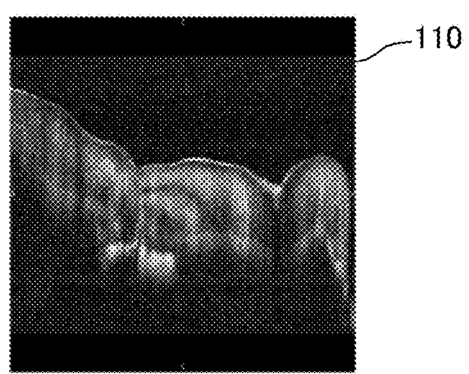
FIG. 7B
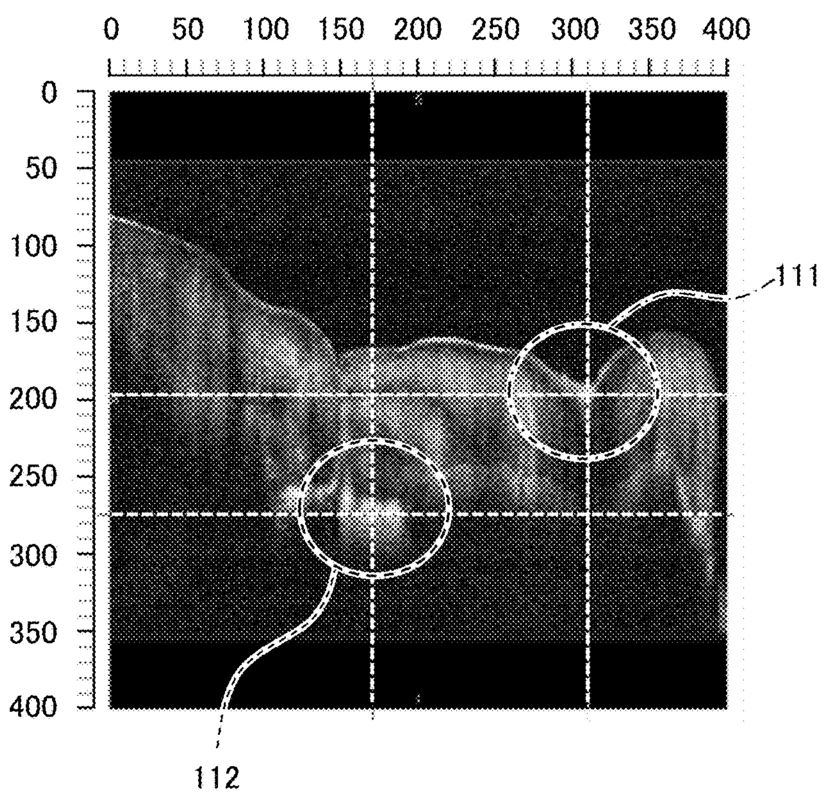
FIG. 7C
| | NAME | CENTER POSITION (X, Y) | DEGREE OF SIMILARITY [%] |
|---|---|---|---|
| 1 | INITIAL CARIES | (310, 195) | 70 |
| 2 | CARIES | (170, 273) | 90 |

20TH IMAGE

| | NAME | CENTER POSITION (X, Y) | DEGREE OF SIMILARITY [%] |
|---|---|---|---|
| 1 | INITIAL CARIES | (0, 0) | 0 |
| 2 | CARIES | (0, 0) | 0 |
| 3 | CRACK | (0, 0) | 0 |

100TH IMAGE

| | NAME | CENTER POSITION (X, Y) | DEGREE OF SIMILARITY [%] |
|---|---|---|---|
| 1 | INITIAL CARIES | (152, 102) | 90 |
| 2 | CARIES | (230, 200) | 20 |
| 3 | CRACK | (0, 0) | 0 |

200TH IMAGE

| | NAME | CENTER POSITION (X, Y) | DEGREE OF SIMILARITY [%] |
|---|---|---|---|
| 1 | INITIAL CARIES | (104, 82) | 10 |
| 2 | CARIES | (250, 198) | 80 |
| 3 | CRACK | (0, 0) | 0 |

300TH IMAGE

| | NAME | CENTER POSITION (X, Y) | DEGREE OF SIMILARITY [%] |
|---|---|---|---|
| 1 | INITIAL CARIES | (92, 73) | 40 |
| 2 | CARIES | (255, 190) | 10 |
| 3 | CRACK | (108, 98) | 80 |

| REGION NAME | LESION NAME | TOMOGRAPHIC POSITION | CENTER POSITION (X, Y) |
|---|---|---|---|
| INITIAL CARIES_1 | INITIAL CARIES | 100 | (152, 102) |
| INITIAL CARIES_2 | INITIAL CARIES | 340 | (110, 35) |
| CARIES_1 | CARIES | 180 | (250, 198) |
| CRACK_1 | CRACK | 300 | (108, 98) |

AI IMAGE DIAGNOSIS DEVICE AND DENTAL OCT IMAGE DIAGNOSIS DEVICE

TECHNICAL FIELD

The present invention relates to an AI image diagnosis apparatus, and particularly to an AI image diagnosis apparatus and dental OCT image diagnosis apparatus that use images captured by a dental OCT device.

BACKGROUND ART

Currently in dentistry, the M.I. treatment method advocated by the FDI (World Dental Federation) in 2000 has gained widespread acceptance. M.I. stands for Minimal Intervention and refers to caries treatment with minimal invasion. A dental OCT (Optical Coherence Tomography) device can obtain high-resolution and high-sensitivity tomographic images of teeth without X-ray exposure. Therefore, the dental OCT image diagnosis apparatus is considered to be an effective diagnostic apparatus for practicing M.I.

For example, the OCT device described in Patent Literature 1 is equipped with a measurement imaging mode that assumes saving of a high-resolution subject image, and a preview imaging mode that quickly displays a low-resolution subject image on a display device as a real-time video. Also, the OCT device described in Patent Literature 2 can perform imaging by switching between a horizontal scan that scans the first scan direction horizontally (transversely) and a vertical scan that scans vertically (longitudinally) on the light irradiation surface of the tooth, using a two-dimensional scanning mechanism.

CITATION LIST

Patent Literature

Patent Literature 1: Japanese Patent No. 5827024
Patent Literature 2: Japanese Patent No. 6712106

SUMMARY OF INVENTION

Technical Problem

The OCT device has the feature of being able to image the inside of a tooth with high resolution and high sensitivity. On the other hand, because of its high sensitivity, changes in the internal state of the tooth other than caries are also imaged, making it difficult to diagnose with OCT images without understanding the structure of the tooth and the characteristics of dental OCT images. In other words, only dentists who have accumulated experience in diagnosing with OCT images can effectively utilize OCT images for dental diagnosis and treatment. Meanwhile, in order to implement the M.I. treatment method by performing early treatment or preventive treatment before symptoms worsen, it is desirable to enable dentists, including those with little experience in diagnosing with OCT images, to effectively utilize OCT images for dental diagnosis and treatment.

The present invention has been made in view of the above circumstances, and an object thereof is to provide an AI image diagnosis apparatus and a dental OCT image diagnosis apparatus that enable dentists to effectively utilize OCT images for dental diagnosis and treatment.

Solution to Problem

To achieve the above object, the AI image diagnosis apparatus according to the present invention is an AI image diagnosis apparatus into which three-dimensional tooth image data captured by a dental OCT device is inputted and which analyzes the inputted three-dimensional tooth image data, wherein a model executor sequentially inputs two-dimensional tomographic image data constituting the diagnostic target three-dimensional tooth image data into a trained model, to thereby obtain, as an execution processing result of the trained model, lesion information data, which is data related to a part identified as a characteristic part such as a lesion in the inputted tomographic image data, for each piece of tomographic image data in the three-dimensional tooth image data, and detect lesions from the inputted three-dimensional tooth image data using the obtained lesion information data, and the trained model is constructed by training of three-dimensional tooth image data of multiple examinees captured by a dental OCT device in the past.

Advantageous Effects of Invention

According to the present invention, dentists, including those with little experience in diagnosing with OCT images, can effectively utilize the dental OCT image diagnosis apparatus for dental diagnosis and treatment.

Also, according to the present invention, by using AI image diagnosis, dental hygienists can perform screening in advance with the dental OCT image diagnosis apparatus, thereby reducing the examination time of dentists.

BRIEF DESCRIPTION OF DRAWINGS

FIG. 7A is a diagram showing an example of tomographic image data to be diagnosed.

FIG. 7B is a schematic diagram of an analyzed image.

FIG. 7C is a diagram showing an example of lesion information data to be outputted.

DESCRIPTION OF EMBODIMENTS

Figure 1:
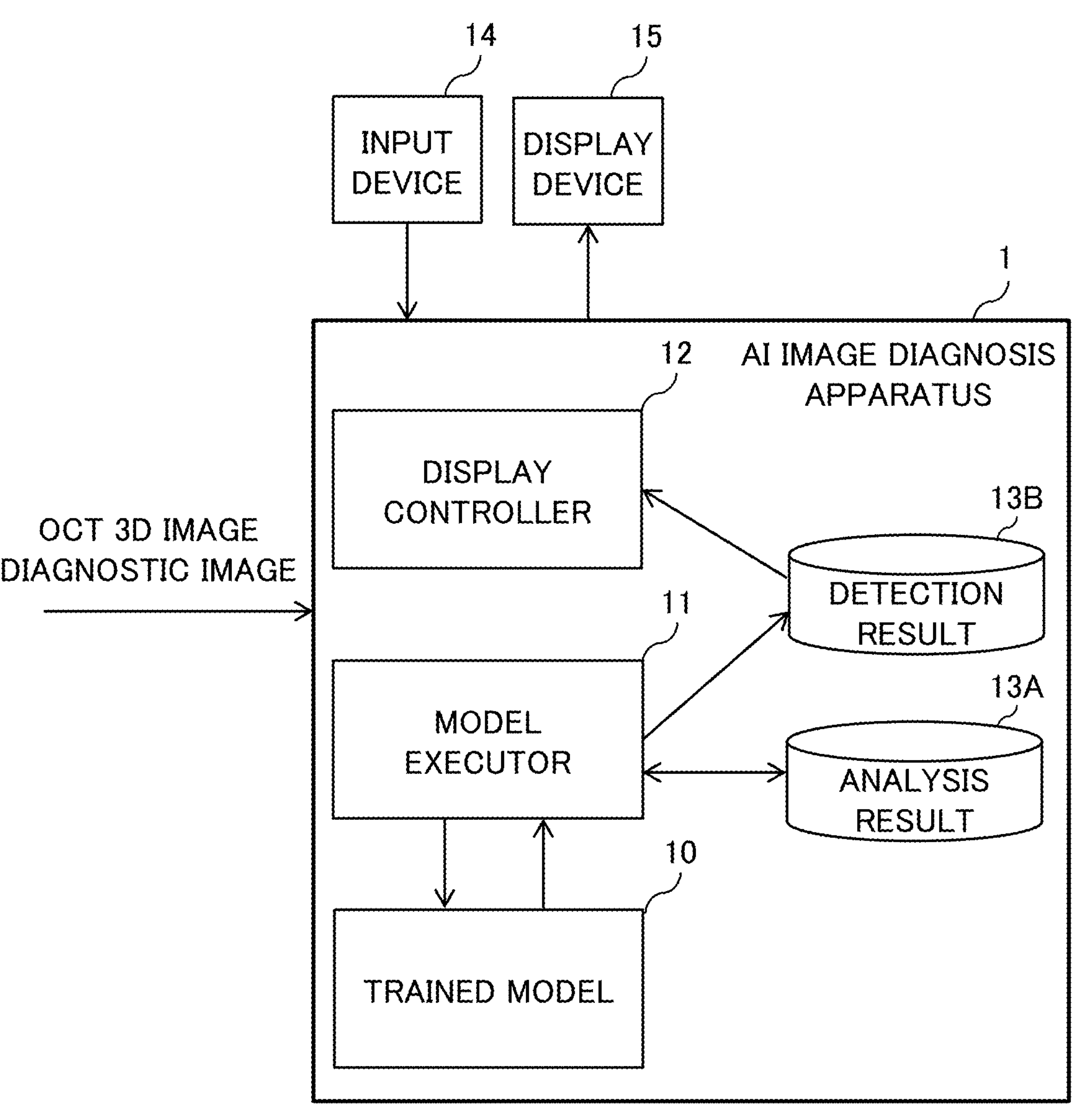
FIG. 1 is a functional block diagram of the AI image diagnosis apparatus according to an embodiment of the present invention.

Embodiments for carrying out the AI image diagnosis apparatus according to the present invention will be described in detail with reference to the drawings. The sizes, positional relationships, etc. of the components shown in each drawing may be exaggerated for the sake of clarity of explanation.

[Configuration of AI Image Diagnosis Apparatus]

The configuration of the AI image diagnosis apparatus according to an embodiment of the present invention will be described with reference to FIG. 1.

The AI image diagnosis apparatus 1 is an apparatus into which three-dimensional tooth image data captured by a dental OCT device is inputted and which analyzes the inputted three-dimensional tooth image data. Hereinafter, the three-dimensional tooth image data (volume data) captured by the dental OCT device is referred to as OCT 3D image. The OCT 3D image inputted to the AI image diagnosis apparatus 1 is a diagnostic image.

The AI image diagnosis apparatus 1 is equipped with a model executor 11. The model executor 11 sequentially inputs two-dimensional tomographic image data constituting the diagnostic target three-dimensional tooth image data into a trained model 10, to thereby obtain, as an execution processing result of the trained model 10, lesion information data for each piece of tomographic image data in the three-dimensional tooth image data, and detect lesions from the inputted three-dimensional tooth image data using the obtained lesion information data. The lesion information data is data related to a part identified as a characteristic part such as a lesion in the inputted tomographic image data.

The trained model 10 is constructed by training of three-dimensional tooth image data of multiple examinees captured by a dental OCT device in the past. As will be described later, the trained model 10 is constructed in the training stage using training data. In the utilization stage of the trained model 10, the AI image diagnosis apparatus 1 performs image diagnosis based on the input OCT 3D images (diagnostic images). As will be described in detail later, regarding the method by which the trained model 10 outputs the lesion information data, it can output numerical values (position coordinates of lesions, etc.) or images (visualized positions of lesions, etc.).

The model executor 11 inputs one piece of tomographic image data from the OCT 3D images (diagnostic images) into the trained model 10, and obtains the lesion information data for that tomographic image data as an analysis result. If the model executor 11 detects multiple lesions in one piece of tomographic image data, it obtains lesion information data for each of them. Even if the model executor 11 does not detect a lesion in one piece of tomographic image data, it obtains lesion information data including information such as a similarity of 0 indicating that no lesion was detected. The model executor 11 inputs all the tomographic image data from the OCT 3D images (diagnostic images) into the trained model 10, and obtains the lesion information data corresponding to each piece of tomographic image data as an analysis result. The diagnostic images include several hundred pieces of tomographic image data, for example. The analysis result 13A shown in FIG. 1 refers to the analysis result for all these tomographic image data. The detection result 13B is information on lesions detected by the model executor 11 from the diagnostic images based on the analysis result 13A. The analysis result 13A and detection result 13B differ depending on the output content of the trained model 10, so that when explaining concrete examples of the trained model, the analysis result 13A and detection result 13B corresponding to that model will also be explained.

The AI image diagnosis apparatus 1 can be equipped with a display controller 12 that functions as a viewer for displaying the OCT 3D images (diagnostic images) on a display device 15 such as a liquid crystal display. The display controller 12 receives information (hereinafter referred to as selected information) determined or selected by the user from an input device 14 operated by the user, such as a mouse or keyboard. The display controller 12 functions as a viewer that displays a predetermined image on the display device 15 such as a liquid crystal display based on the OCT 3D images (diagnostic images) and detection result 13B. The selected information from the user operation and the predetermined image displayed on the display device 15 differ depending on the output content of the trained model 10, and will be explained together with the selected information and image corresponding to that model when explaining concrete examples of the trained model 10.

[Training Stage]

Next, the generation of training data and the construction of the model in the training stage will be described with reference to FIG. 2 and FIG. 3.

Figure 2:
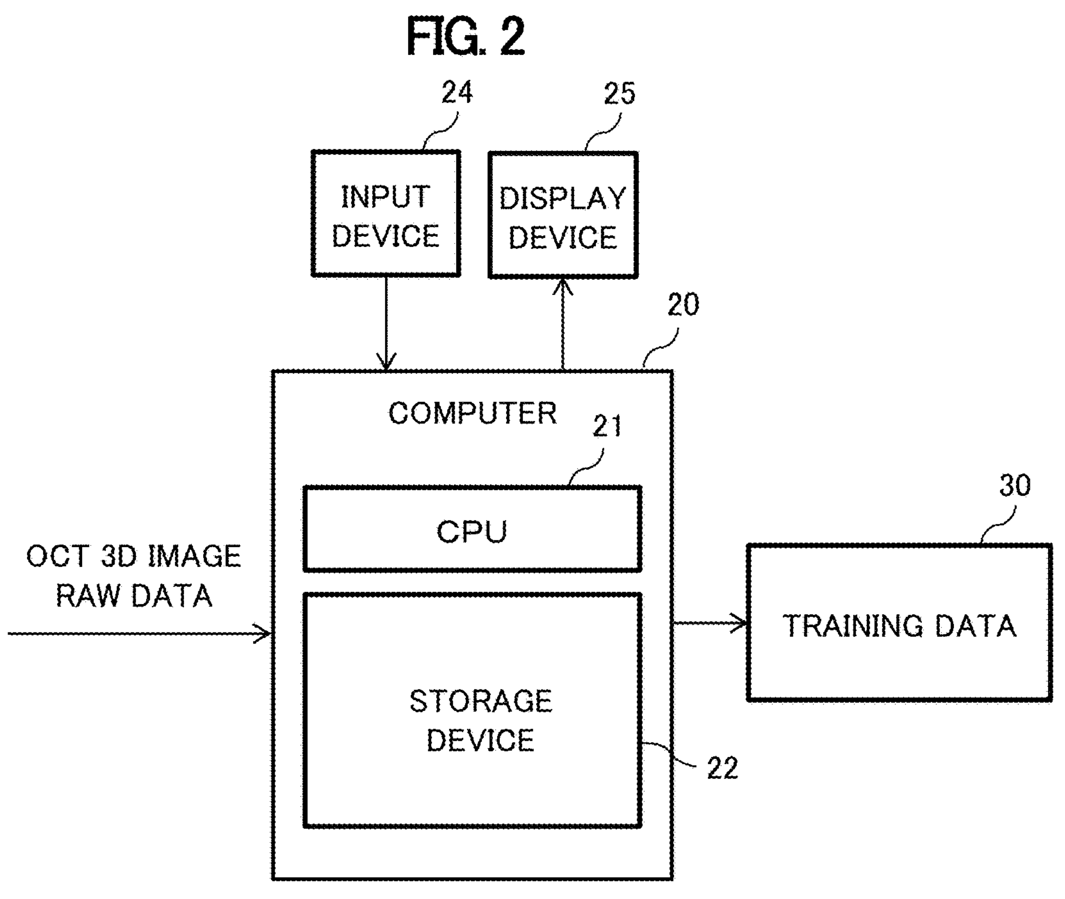
FIG. 2 is a conceptual diagram of the work of generating training data used for training.

FIG. 2 is a conceptual diagram of the work of generating training data used for training. The computer 20 shown in FIG. 2 is equipped with a CPU (Central Processing Unit) 21 and a storage device 22, and functions as a viewer. The CPU 21 operates based on a program stored in the storage device 22, and also controls the input device 24 and the display device 25. The storage device 22 is equipped with a ROM (Read Only Memory), RAM (Random Access Memory), HDD (Hard Disk Drive), etc. The storage device 22 stores various programs such as software necessary for labeling tomographic image data. The input device 24 is for inputting instructions from the user, and includes a mouse, keyboard, etc. The display device 25 displays tomographic images, and includes, for example, a liquid crystal display. On the screen of the display device 25, windows, icons, buttons, etc. are displayed, and the operator (dentist) can perform operations to select them with the input device 24.

The operator (dentist) uses the viewer (computer 20) to check the tomographic images of tooth images (OCT 3D images) captured by the dental OCT device and look for lesion images (characteristic parts of lesions). The operator (dentist) labels the tomographic images in which characteristic parts of lesions are found in order to classify the characteristic parts of lesions. Specifically, the operator (dentist) creates training data and saves it by adding to the tomographic image data a label created by performing an input operation such as entering the name of the lesion, or a label selected from among multiple prepared labels. This work of labeling is called annotation. The training data 30 shown in FIG. 2 and FIG. 3 schematically shows a collection of tomographic images that have been labeled, for example, a collection of 1000 tomographic images.

The training data can include at least one of A-plane tomographic image data, L-plane tomographic image data, S-plane tomographic image data, en-face image data, and three-dimensional image data composed of several consecutive pieces of tomographic image data. Here, A, L, and S represent different cross-sectional directions. Specifically, the A-plane is a cross-section parallel to a plane specified by both a B-axis direction orthogonal to the A-axis direction, which is an irradiation direction of OCT laser light on the tooth, and the A-axis direction. The L-plane is a cross-section parallel to a plane specified by both a V-axis direction, orthogonal to the A-axis direction and the B-axis direction, and the A-axis direction. The S-plane is a cross-section parallel to a plane specified by both the B-axis direction and the V-axis direction. The en-face image data is image data synthesized from information on a surface of the tooth irradiated with the OCT laser light and information on the A-axis direction. This en-face image data also synthesizes internal information that does not originally appear on the outer surface.

It is preferred that the training data includes at least the A-plane tomographic image data and the L-plane tomographic image data. For one lesion, there are three images, namely those of A-plane, L-plane, and S-plane, so that these three pieces of tomographic image data can be labeled and all used as training data.

The label added to the training data includes the name of the lesion. The characteristic part of the lesion in the tomographic image (hereinafter referred to as the lesion characteristic part) is an image of the lesion, for example, an image showing at least one of initial caries (Ce), caries (C1 or higher), secondary caries, root surface caries, cracks, fractures, and attrition.

The label added to the training data can include the type of tooth in addition to the name of the lesion. The type of tooth can be broadly classified into molars, incisors, and canines. From another perspective, the type of tooth can also be divided into permanent teeth and deciduous teeth. These types of teeth can also use the dental formula. For example, if using the FDI (two-digit system) dental formula, just entering a two-digit number can identify whether it is a permanent tooth or a deciduous tooth, and also whether it is a molar, incisor, or canine. Teeth differ in external shape and internal structure depending on the type, so that by including the type of tooth in the label added to the training data, the presence or absence of lesions can be determined even more appropriately.

Also, the label added to the training data can include the type of image data. The types of image data include A-plane tomographic image, L-plane tomographic image, S-plane tomographic image, en-face image, and 3D image. These can be identified with 2 characters or less, such as A, L, S, en, 3D.

Furthermore, the label added to the training data can include names other than lesions. In this case, when the operator (dentist) finds an image of a characteristic part other than a lesion (hereinafter referred to as a non-lesion characteristic part) such as dental plaque in the tomographic image, the operator enters dental plaque as a name other than a lesion in the label. The non-lesion characteristic part in the tomographic image is an image other than a lesion, for example, an image showing at least one of metal, ceramic, resin, dental plaque, and saliva bubbles. Although these are images other than lesions, by including names other than lesions in the label added to the training data, the presence or absence of lesions can be determined even more appropriately.

Figure 3:
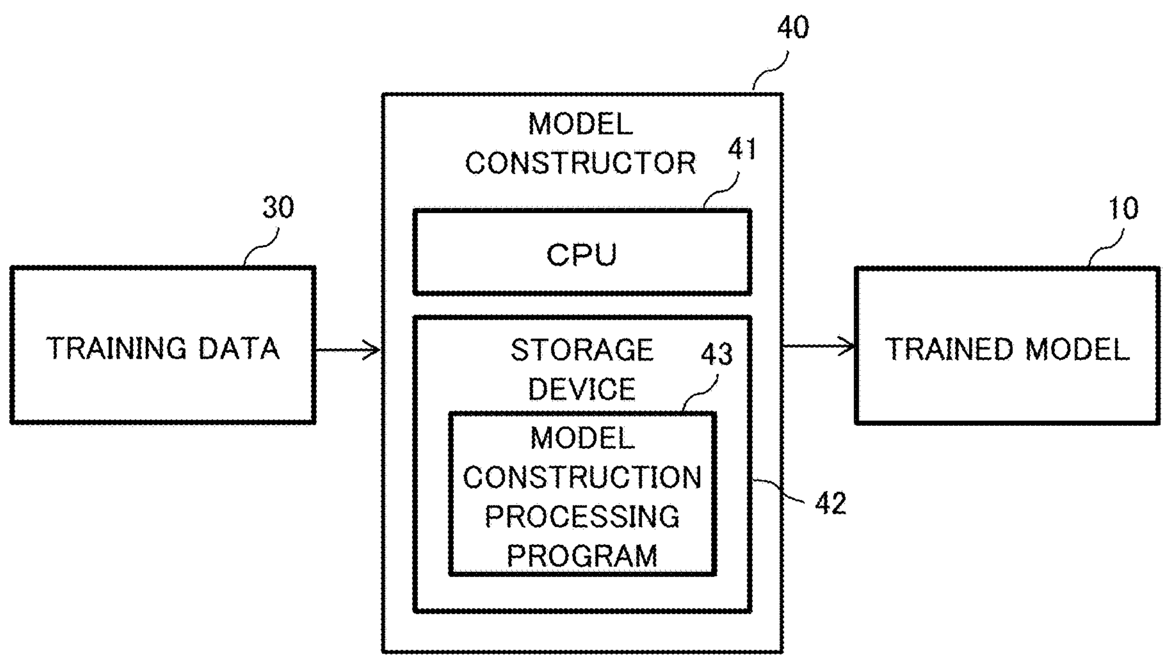
FIG. 3 is a conceptual diagram of the work of constructing a trained model in the training stage.

FIG. 3 is a conceptual diagram of the work of constructing a trained model in the training stage. The model constructor 40 shown in FIG. 3 is equipped with a CPU 41 and a storage device 42, and functions as a training device. The CPU 41 operates based on the model construction processing program 43 stored in the storage device 42. The model construction processing program 43 schematically shows a program that executes a machine learning algorithm such as a neural network. By inputting the training data 30 to the model constructor 40 and training it, the trained model 10 can be constructed.

When creating the training data 30, the operator (dentist) found the characteristic part (image of lesion, etc.) in the tomographic image and labeled it. In contrast, the trained model finds the characteristic part (image of lesion, etc.) in the inputted tomographic image and outputs lesion information data.

[Operation of AI Image Diagnosis Apparatus]

Figure 4:
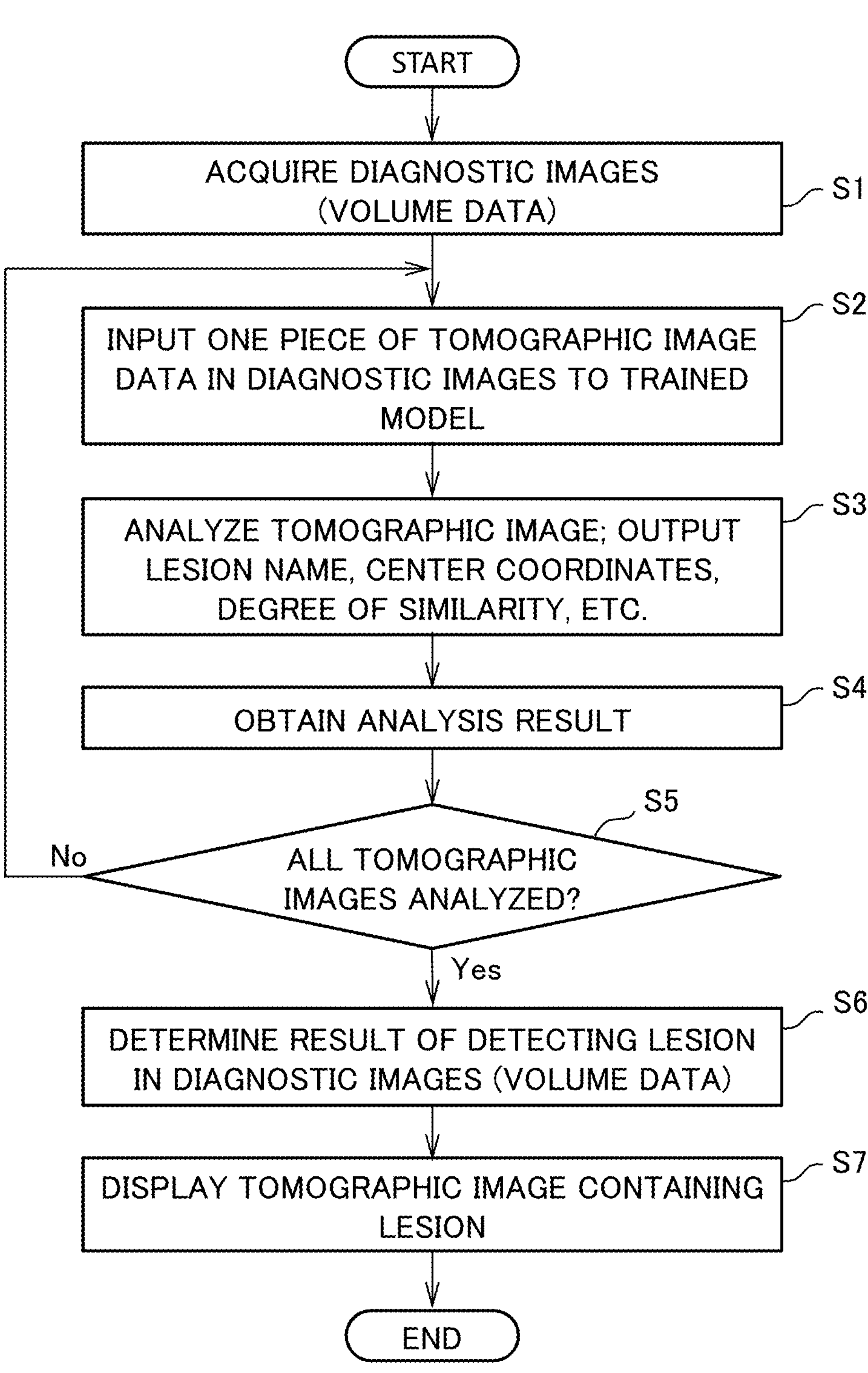
FIG. 4 is a flowchart showing the flow of image analysis processing of the AI image diagnosis apparatus according to an embodiment of the present invention.

Next, the flow of image analysis processing by the AI image diagnosis apparatus 1 will be described with reference to FIG. 4 (referring to FIG. 1 as appropriate). FIG. 4 is a flowchart showing the flow of image analysis processing of the AI image diagnosis apparatus 1. As shown in FIG. 4, first, an unillustrated dental OCT device acquires diagnostic images (volume data) (step S1). Then, the AI image diagnosis apparatus 1 uses the model executor 11 to input one piece of tomographic image data from the diagnostic images to the trained model 10 (step S2). The tomographic image data from the diagnostic images can be obtained from an external device each time, or can be inputted from data stored in the storage device of the AI image diagnosis apparatus 1.

Then, the trained model 10 analyzes the tomographic image and outputs, as an analysis result, information such as the name of the lesion, center coordinates, and degree of similarity found in the tomographic image (step S3). Then, the model executor 11 obtains the analysis result (step S4). Then, the model executor 11 determines whether all tomographic images have been analyzed (step S5). If not all tomographic images have been analyzed (step S5: No), the model executor 11 returns to step S2. On the other hand, if all tomographic images have been analyzed (step S5: Yes), the model executor 11 determines the lesion detection result 13B in the diagnostic images (volume data) based on the analysis results 13A obtained so far (step S6). Then, if the AI image diagnosis apparatus 1 is equipped with the display controller 12, it receives the user's selected information from the input device 14. Then, the display controller 12 searches for the tomographic image containing the lesion selected by the user from the diagnostic images (volume data) based on the detection result 13B, and displays the tomographic image on the display device 15 (step S7).

[Trained Model Construction Processing]

Figure 5:
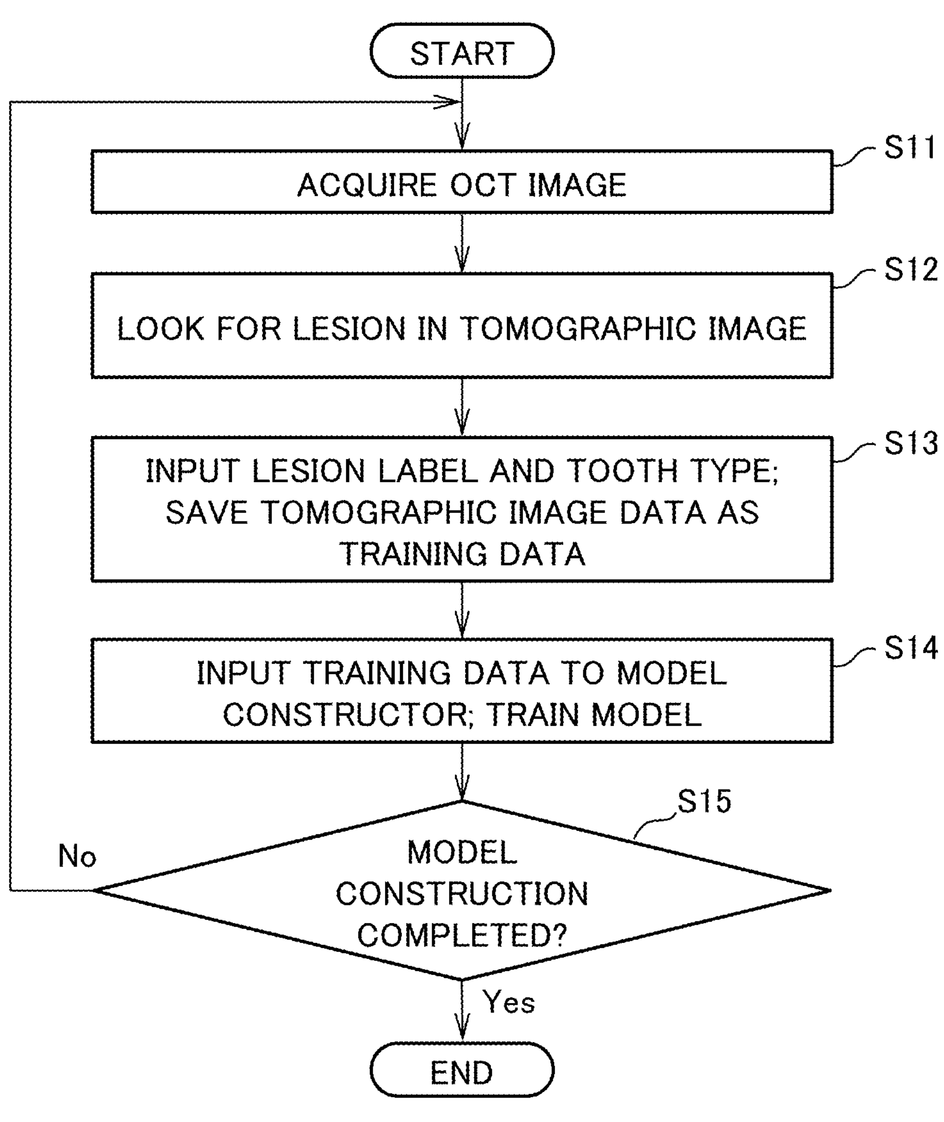
FIG. 5 is a flowchart showing the flow of a trained model construction process.

Next, as an example, the flow of processing when the operator performs the generation of training data and the construction of the trained model as a series of work will be described with reference to FIG. 5 (referring to FIGS. 2 and 3 as appropriate). FIG. 5 is a flowchart showing the flow of the trained model construction process. As shown in FIG. 5, first, the computer 20 functioning as a viewer acquires an OCT image (step S11). This OCT image is raw data of a tomographic image in the OCT 3D image captured in advance for generating training data. This tomographic image data can be data acquired from an external device each time, or data stored in the storage device 22 of the computer 20. Then, the operator (dentist) checks the tomographic image with the viewer and looks for lesions in the tomographic image (step S12). Then, for the tomographic image in which a lesion is found, the operator (dentist) performs input of a label classified for each lesion and input of the tooth type (dental formula), and saves the labeled tomographic image data as training data 30 (step S13). Then, the operator inputs the training data 30 to the model constructor 40 and trains the model (step S14). When the model construction is completed (step S15: Yes), the model at that time is constructed as the trained model 10 and the process ends. On the other hand, if the model construction is not completed (step S15: No), it returns to step S11. The processing in step S14 is repeated until the training on, for example, 1000 labeled tomographic images is finished.

[Output Method of Trained Model]

Hereinafter, the trained model 10 that outputs numerical values (position coordinates of lesions, etc.) as lesion information data will be referred to as the first trained model. Also, the trained model 10 that outputs images (visualized positions of lesions, etc.) as lesion information data will be referred to as the second trained model. The first trained model and the second trained model will be described in order.

<First Trained Model>

The first trained model is constructed by performing machine learning so as to use, as first training data, tomographic image data containing lesion characteristic parts among the tomographic image data constituting the three-dimensional tooth image data captured by a dental OCT device in the past, search for a lesion characteristic part from the inputted tomographic image data, and output lesion information data.

The lesion information data includes at least a name of each characteristic part, a center position indicating coordinates of a point with the highest degree of similarity to the characteristic part assigned to each point constituting an image in the tomographic image data, and a degree of similarity assigned to the point indicating the center position. The "name of the characteristic part" in the lesion information data is, for example, initial caries, caries, etc., and is the same as the name entered in the label added to the training data described above. The "degree of similarity" is the degree of similarity to the lesion image, indicating the probability of matching the lesion.

Figure 6A:
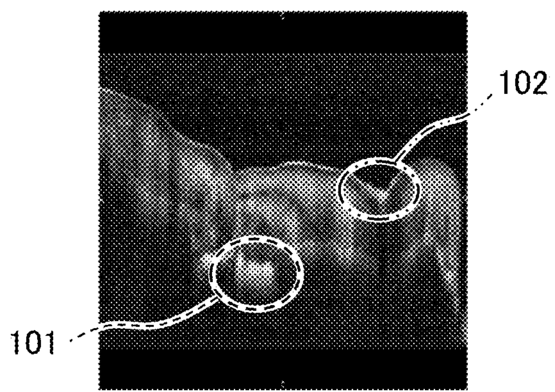
FIG. 6A is a diagram showing an example of training data.
Figure 6B:
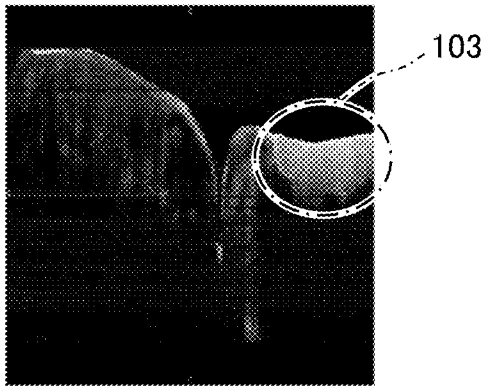
FIG. 6B is a diagram showing an example of training data.
Figure 6C:
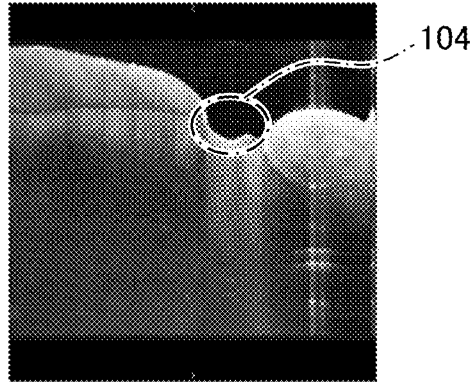
FIG. 6C is a diagram showing an example of training data.

In the training stage, the first trained model (trained model 10) is constructed by inputting the training data 30 to the model constructor 40 (FIG. 3) and training the model. FIGS. 6A to 6C are diagrams showing examples of training data used in the training stage. The training data shown in FIG. 6A has oval marks 101 and 102 added to the tomographic image. The mark 101 was added by the dentist in the training data generation stage to surround the lesion found in the tomographic image of the molar, indicating that the label "caries" was inputted for the lesion found. The mark 102 was similarly added to the lesion found, indicating that the label "initial caries" was inputted. The training data shown in FIG. 6B is an example of a non-lesion image. The mark 103 was added to the non-lesion image found in the tomographic image of the molar, indicating that the label "resin" was inputted. The mark 104 in the training data shown in FIG. 6C was added to the lesion found in the tomographic image of the anterior tooth, indicating that the label "root surface caries" was inputted.

Next, the input/output data of the first trained model in the utilization stage will be described with reference to FIGS. 7A to 7C. FIG. 7A is a diagram showing an example of tomographic image data to be diagnosed. FIG. 7B shows a schematic diagram of the image analyzed when the tomographic image 110 shown in FIG. 7A is inputted to the first trained model. FIG. 7C shows an example of the lesion information data outputted from the first trained model at this time. The conceptual diagram in FIG. 7B is an enlarged view of the tomographic image 110 shown in FIG. 7A, with the addition of the areas 111 and 112 where images presumed to be lesions were detected, and the horizontal axis (X-axis) and vertical axis (Y-axis). The scale of the vertical and horizontal axes represents position coordinates. As an example, the total number of tomographic positions constituting the diagnostic images is 400. The lesion information data shown in FIG. 7C indicates that the image in area 111 is determined to be initial caries with a similarity of 70%, and the coordinates (310, 195) of the point with the highest similarity of initial caries are obtained as the center position. Similarly, it indicates that the image in area 112 is determined to be caries with a similarity of 90%.

If the first trained model finds multiple lesions in one piece of tomographic image data, it outputs the above lesion information data for each lesion.

If the first trained model finds the same type of lesion in the diagnostic images, it assigns distinguishable names. For example, for caries, it may distinguish them as "caries_01", "caries_02".

The first trained model can determine lesions by searching one piece of tomographic image data, but it can also determine lesions from the search results using several consecutive pieces of tomographic image data.

The model executor 11 of the AI image diagnosis apparatus 1 obtains the lesion information data from the first trained model.

The above first trained model was described as being constructed by machine learning using tomographic image data containing lesion characteristic parts as the first training data, but it is not limited to this. The first trained model can be constructed by machine learning using tomographic image data containing lesion characteristic parts and tomographic image data containing non-lesion characteristic parts as training data. In this variation, the first trained model uses, as the second training data, tomographic image data containing lesion characteristic parts and tomographic image data containing non-lesion characteristic parts among the tomographic image data constituting the three-dimensional tooth image data captured by a dental OCT device in the past. In this case, the first trained model is constructed by machine learning so as to search for lesion characteristic parts and non-lesion characteristic parts from the inputted tomographic image data and output lesion information data.

<Second Trained Model>

The second trained model is constructed by performing machine learning so as to use, as first training data, tomographic image data containing lesion characteristic parts among the tomographic image data constituting the three-dimensional tooth image data captured by a dental OCT device in the past, search for a lesion characteristic part from the inputted tomographic image data, and generate image data representing the degree of matching by replacing the degree of similarity to the characteristic part assigned to each point constituting the image in the tomographic image data with a pixel value, to thereby output the position of the characteristic part by visualization thereof. The lesion information data includes at least the name of the characteristic part and the image representing the degree of matching. The image representing the degree of matching is image data in which the degree of similarity of the lesion is replaced with a pixel value (numerical value representing brightness). The second trained model makes the pixel value larger (brighter) for higher degrees of similarity. In other words, the image representing the degree of matching is an image in which the part presumed to be a lesion is bright and the part not presumed to be a lesion is dark.

In the training stage, the second trained model (trained model 10) is constructed by inputting the training data 30 to the model constructor 40 (FIG. 3) and training the model. FIGS. 6A to 6C show examples of training data used in the training stage.

Figure 8:
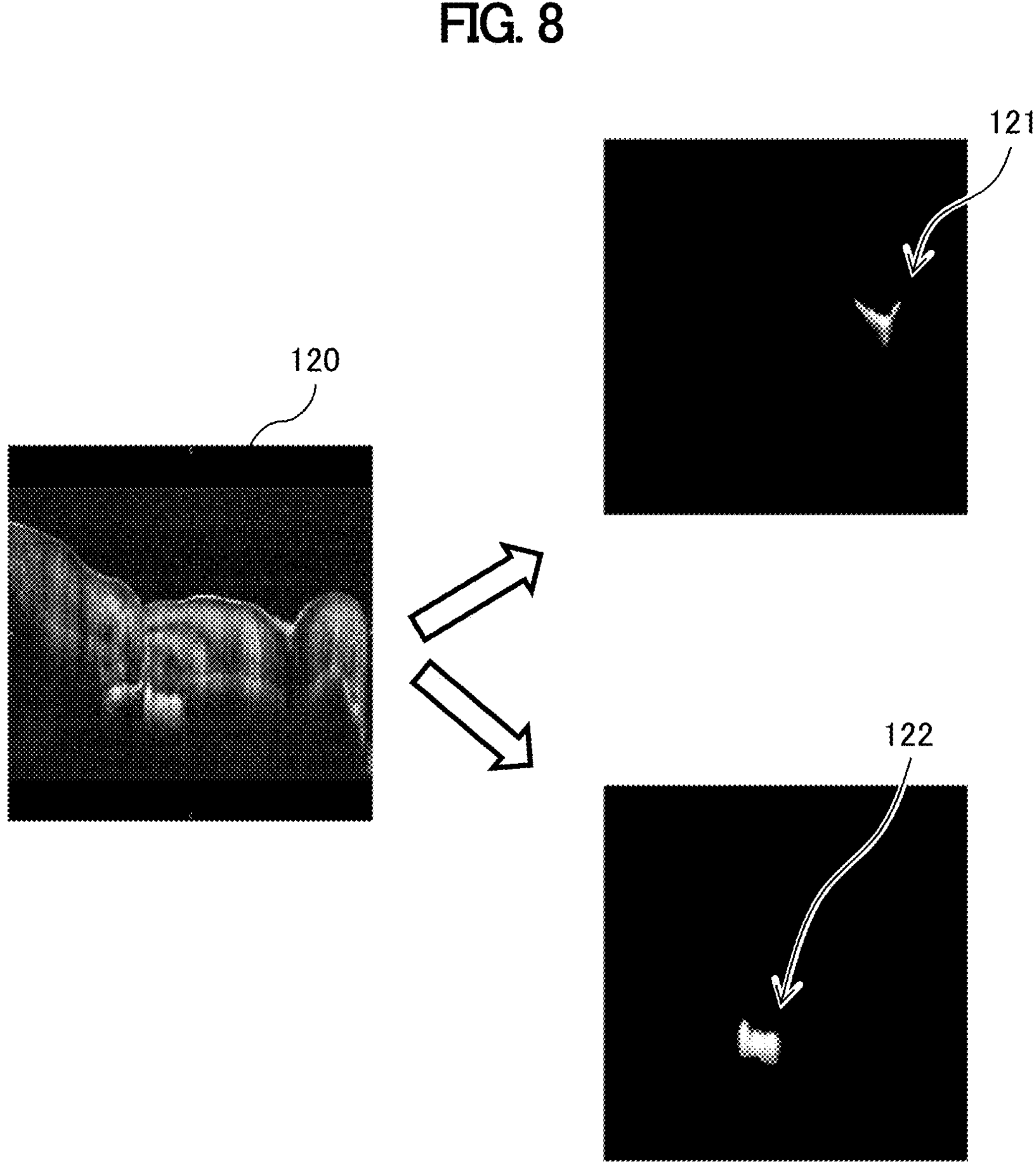
FIG. 8 is a diagram showing input data and two pieces of output data of the second trained model, respectively.

Next, the input/output data of the second trained model in the utilization stage will be described with reference to FIG. 8. The tomographic image 120 shown in FIG. 8 shows an example of tomographic image data to be diagnosed. The images representing the degree of matching output when this tomographic image 120 is inputted to the second trained model are the two images shown on the right side of the tomographic image 120 in FIG. 8. The output image arranged at the top in FIG. 8 is an image representing the degree of matching of initial caries 121, and the output image arranged at the bottom is an image representing the degree of matching of caries 122.

The second trained model can determine lesions by searching one piece of tomographic image data, but it can also determine lesions from the search results using several consecutive pieces of tomographic image data.

The model executor 11 of the AI image diagnosis apparatus 1 determines the name of the characteristic part included in the lesion information data as selected information based on the lesion information data for each piece of tomographic image data in the three-dimensional tooth image data obtained from the second trained model. Then, the model executor 11 reconstructs the image representing the degree of matching included in the lesion information data for each name of the characteristic part, thereby generating a three-dimensional image of the characteristic part. Then, the model executor 11 uses this generated three-dimensional image of the characteristic part as a detection result 13B of lesions in the three-dimensional tooth image data.

When replacing the degree of similarity to a characteristic part with a pixel value, the second trained model can generate the image representing the degree of matching by processing to convert a pixel value of pixels with a degree of similarity smaller than a predetermined threshold value to 0. In this case, the model executor 11 of the AI image diagnosis apparatus 1 obtains from the second trained model the image subjected to the processing of converting the pixel value of pixels with a degree of similarity smaller than the threshold value to 0 as the image representing the degree of matching. Thereby, in the image representing the degree of matching, the parts with a low degree of similarity to the lesion in the tomographic image where the lesion was found all become completely black. Therefore, the image representing the degree of matching becomes easier to view.

The above second trained model was described as being constructed by machine learning using tomographic image data containing lesion characteristic parts as the first training data, but it is not limited to this. The second trained model can be constructed by machine learning using tomographic image data containing lesion characteristic parts and tomographic image data containing non-lesion characteristic parts as training data. In this variation, the second trained model uses, as the second training data, tomographic image data containing lesion characteristic parts and tomographic image data containing non-lesion characteristic parts among the tomographic image data constituting the three-dimensional tooth image data captured by a dental OCT device in the past. In this case, the second trained model is constructed by machine learning so as to search for lesion characteristic parts and non-lesion characteristic parts from the inputted tomographic image data, and generate image data representing the degree of matching by replacing the degree of similarity to the characteristic part assigned to each point constituting the image in the tomographic image data with a pixel value, to thereby output the position of the characteristic part by visualization thereof.

Example 1

Next, an example (Example 1) in which the AI image diagnosis apparatus 1 detects lesions in the input OCT 3D images (diagnostic images) using the above-described first trained model will be described. The model executor 11 of the AI image diagnosis apparatus 1 according to Example 1 graphs a relationship between the tomographic position and the degree of similarity of the characteristic part for each characteristic part based on the lesion information data for each piece of tomographic image data in the three-dimensional tooth image data obtained from the first trained model. Then, the model executor 11 finds regions where the degree of similarity continuously exceeds a predetermined threshold value over consecutive tomographic positions on the graph. Then, the model executor 11 determines a region name as selected information for each region. Then, for each region where the region name has been determined, the model executor 11 generates a detection result of lesions in the three-dimensional tooth image data by associating the name of the characteristic part, the tomographic position with the highest degree of similarity in the region, and the center position at the tomographic position with the highest degree of similarity in the region, with the region name.

Then, in the case where the AI image diagnosis apparatus 1 according to Example 1 includes the display controller 12, the region name is inputted to the display controller 12 as selected information by user operation. Subsequently, the display controller 12 extracts the tomographic image data corresponding to the inputted region name from the inputted three-dimensional tooth image data based on the lesion detection result 13B generated by the model executor 11, and displays the tooth image including the tomographic image on the display device 15.

Figure 9:
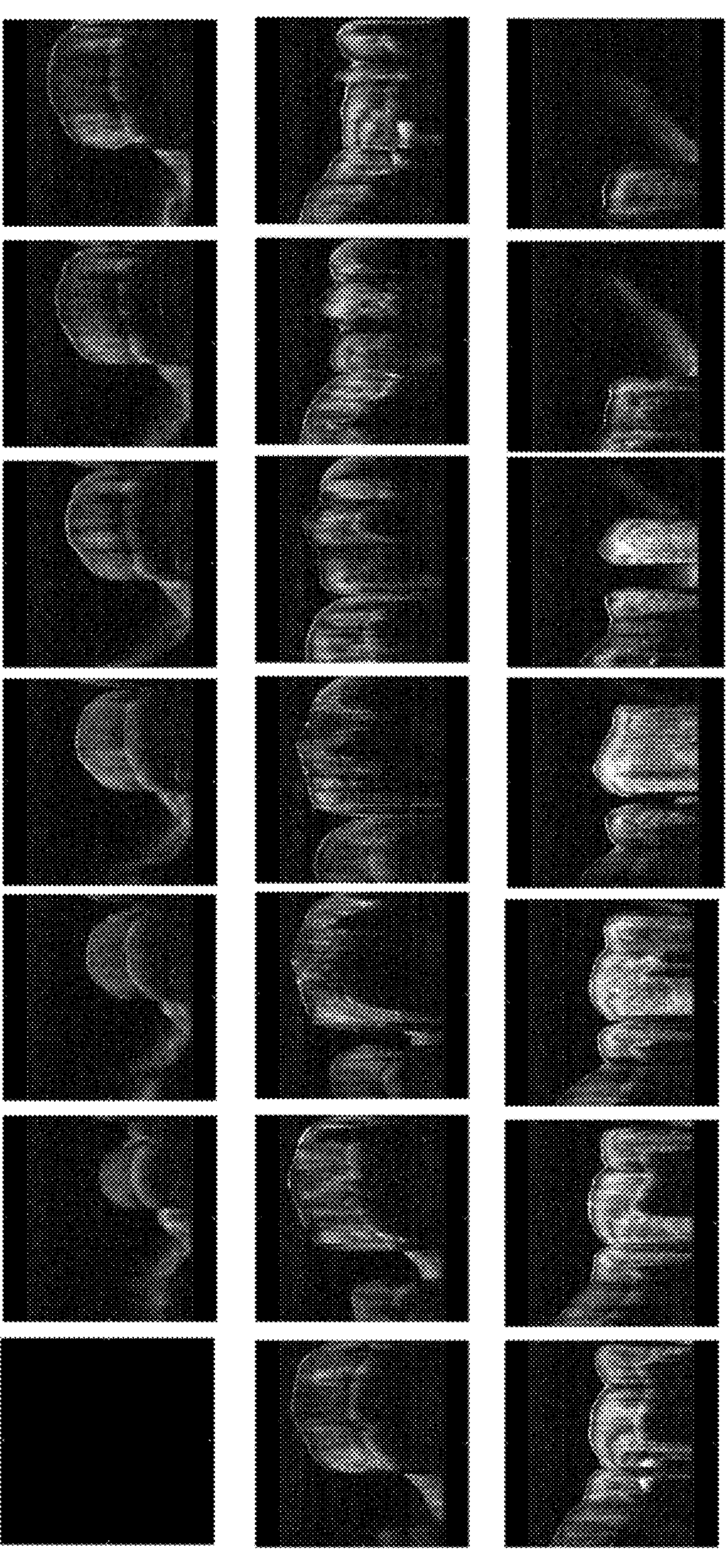
FIG. 9 is a diagram showing an example of tomographic image data of 3D image data acquired by a dental OCT device in the A-plane, respectively.

Specifically, the model executor 11 of the AI image diagnosis apparatus 1 according to Example 1 sequentially inputs the multiple pieces of A-plane tomographic image data in the 3D image data acquired by the dental OCT device to the first trained model in order from front to back (anteroposterior direction). FIG. 9 shows an example of the A-plane tomographic image data sequentially inputted to the first trained model. The tomographic image data shown in FIG. 9 and the training data in the training stage are those captured in the measurement imaging mode of the dental OCT device, which assumes the saving of high-resolution subject images. The model executor 11 can input all the A-plane tomographic image data to the first trained model in order, or can input them to the first trained model every few images. Thereby, Example 1 can process the 3D image data at high speed.

Figure 10A:
FIG. 10A is a diagram showing an example of a 3D image displayed on a screen.

FIG. 10A shows an example of a screen displaying a 3D image captured by a dental OCT device. In FIG. 10A, the image on the left is a 3D image. The four images shown divided into four on the right side in FIG. 10A are, respectively, an A-plane tomographic image (upper left), an L-plane tomographic image (upper right), an S-plane tomographic image (lower right), and an en-face image (lower left).

In the training stage, if the images as training data include A-plane tomographic images and L-plane tomographic images, in the utilization stage, the user can select either the tomographic images constructed by horizontal scanning or the tomographic images constructed by vertical scanning, so that the usability is improved.

Figure 10B:
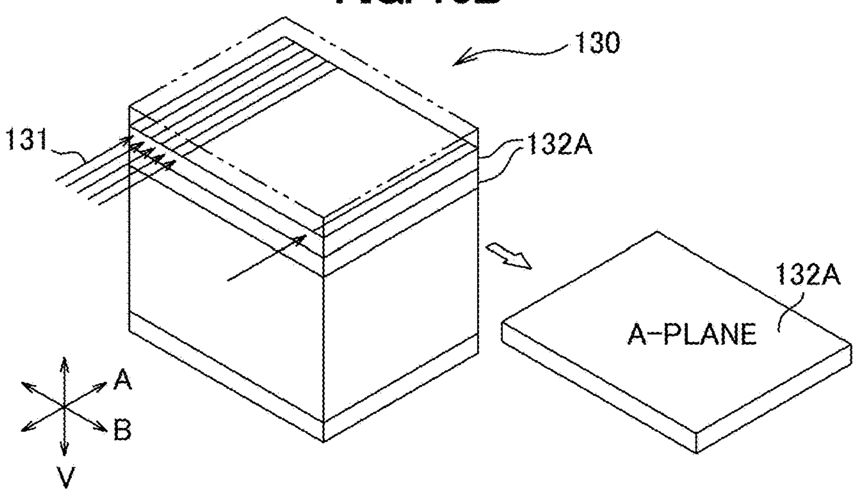
FIG. 10 is a schematic diagram of a molar tooth in the case of horizontal scanning.
FIG. 10C is a schematic diagram of a molar tooth in the case of vertical scanning.
Figure 10C:
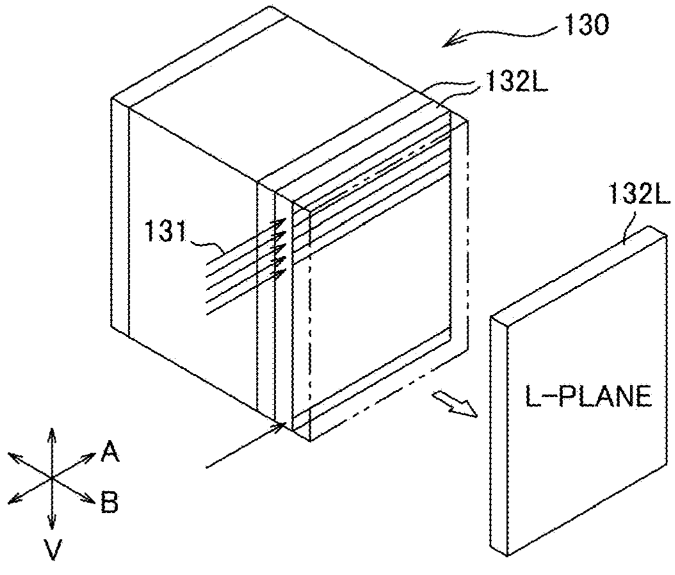

Horizontal scanning and vertical scanning will be described with reference to FIGS. 10B and 10C. The dental OCT device obtains A-scan data 131 having a large number of data acquisition points for each line by irradiating the tooth with laser light. During horizontal scanning imaging, as shown in FIG. 10B, the dental OCT device obtains A-plane tomographic image data 132A by writing multiple pieces of A-scan data 131 along the B-axis direction in the 3D coordinate space. Then, the dental OCT device constructs the 3D image data 130 by stacking this tomographic image data 132A in the V-axis direction. During vertical scanning imaging, as shown in FIG. 10C, the dental OCT device obtains L-plane tomographic image data 132L by writing multiple pieces of A-scan data 131 along the V-axis direction in the 3D coordinate space. Then, the dental OCT device constructs the 3D image data 130 by stacking this tomographic image data 132L in the B-axis direction. For example, when a dentist diagnoses root surface caries or gingiva, it is more suitable to use tomographic image data constructed by vertical scanning rather than horizontal scanning. The details are described in Patent Literature 2, so that further explanation is omitted.

The model executor 11 of the AI image diagnosis apparatus 1 according to Example 1 accepts an instruction of either horizontal scanning or vertical scanning by user operation, for example. At this time, when the model executor 11 accepts the instruction of horizontal scanning, it inputs the A-plane tomographic image data to the first trained model and executes arithmetic processing of the first trained model. Also, when the model executor 11 accepts the instruction of vertical scanning, it inputs the L-plane tomographic image data to the first trained model and executes arithmetic processing of the first trained model.

Alternatively, the model executor 11 can determine the scanning direction based on the input information. In this case, for example, the model executor 11 determines scanning direction information of the dental OCT device when imaging, which is included in the inputted three-dimensional tooth image data. At this time, when the model executor 11 determines that the inputted three-dimensional tooth image data includes horizontal scanning information, it inputs the A-plane tomographic image data to the first trained model and executes arithmetic processing of the first trained model. Also, when the model executor 11 determines that the inputted three-dimensional tooth image data includes vertical scanning information, it inputs the L-plane tomographic image data to the first trained model and executes arithmetic processing of the first trained model.

Figures 11A, 11B:
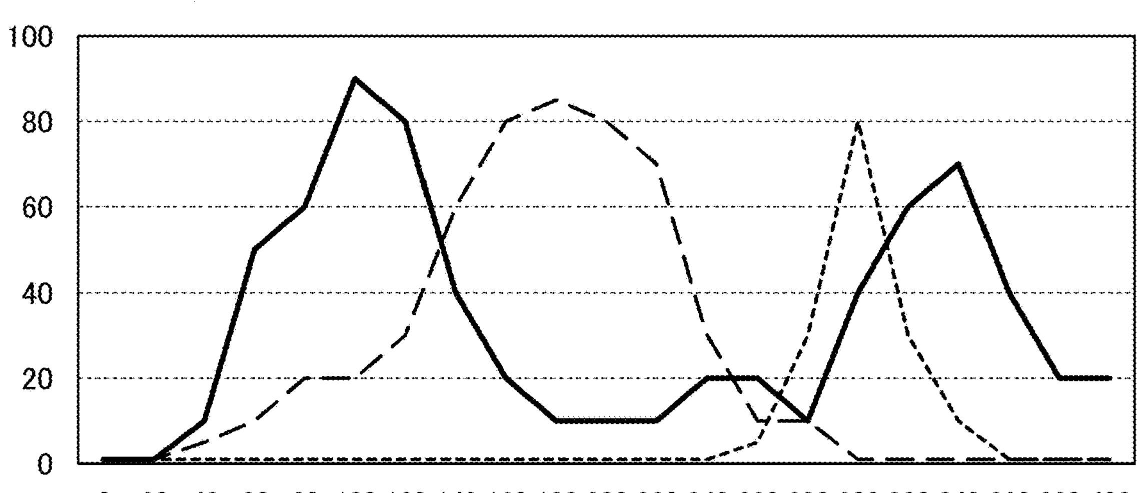
FIG. 11A is a diagram showing an example of lesion information data obtained by the first trained model.
FIG. 11B is a graph showing an example of the relationship between the tomographic position and the degree of similarity of the characteristic part.

The first trained model finds lesions from the inputted tomographic image data and outputs lesion information data (name of characteristic part, center position, degree of similarity). FIG. 11A shows an example of the lesion information data obtained by analyzing all the tomographic image data with the first trained model, assuming the total number of tomographic positions constituting the diagnostic images is 400, for example.

FIG. 11A shows the lesion information data for the 20th, 100th, 200th, and 300th piece of tomographic image data out of the total 400 tomographic positions, respectively. In this example, initial caries, caries, and cracks are found as lesions throughout all the tomographic image data, but for example, these lesions were not found in the 20th piece of tomographic image data.

FIG. 11B shows an example of a graph in which the model executor 11 of the AI image diagnosis apparatus 1 according to Example 1 finds the relationship between the tomographic position and the degree of similarity of the characteristic part for each characteristic part based on the lesion information data for all these tomographic image data. In FIG. 11B, the horizontal axis represents the tomographic position, and the vertical axis represents the degree of similarity (%). The thick line shows initial caries (Ce), the dashed line shows caries (C1 or higher), and the dotted line shows cracks, respectively. The graph of the dashed line and the graph of the dotted line have a shape with one peak. On the other hand, the graph of the thick line (caries) has a shape with two peaks, suggesting that caries may have been found in two locations.

Figures 12A, 12B:
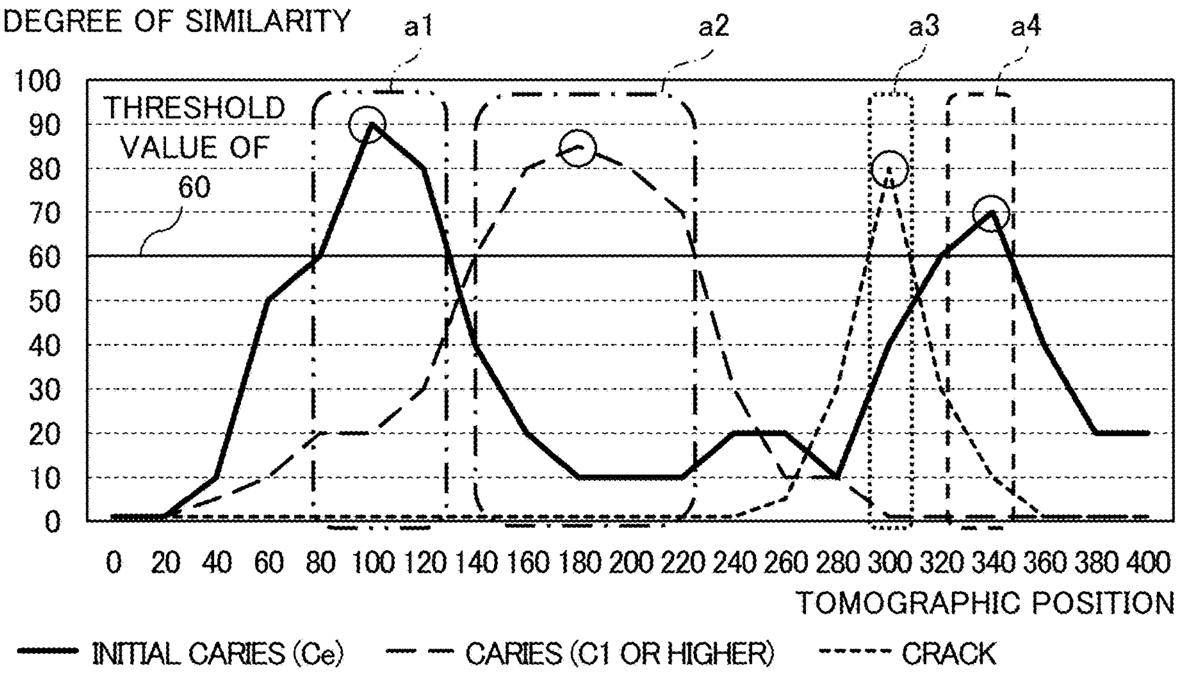
FIG. 12A is a diagram showing a region where the degree of similarity exceeds a predetermined threshold value.
FIG. 12B is a diagram showing a lesion detection result in the three-dimensional tooth image data.

The model executor 11 of the AI image diagnosis apparatus 1 according to Example 1 finds regions a1, a2, a3, and a4 where the degree of similarity continuously exceeds a predetermined threshold value over consecutive tomographic positions on the graph, as shown in FIG. 12A. Then, the model executor 11 determines a region name as selected information for each found region. In this example, the boundary of the region was determined by setting the threshold value of the degree of similarity to 60. The name of region a1 is “initial caries_1”, the name of region a2 is “caries_1”, the name of region a3 is “crack_1”, and the name of region a4 is “initial caries_2”. These region names are used as selected information in the processing of the display controller 12 of the AI image diagnosis apparatus 1 according to Example 1.

The model executor 11 of the AI image diagnosis apparatus 1 according to Example 1 determines a representative point of the region for each region where the region name has been determined. The representative point of the region is characterized by the tomographic position with the highest degree of similarity in that region and the center position at the tomographic position with the highest degree of similarity. By associating the representative point of that region with the region name (selected information), the model executor 11 generates the detection result 13B (see FIG. 1) of lesions in the three-dimensional tooth image data. FIG. 12B shows an example of the detection result 13B. In FIG. 12B, for example, the data with the region name “initial caries_1” indicates that the center position of the initial caries in region a1 is at the coordinates (152, 102) of the tomographic image data at tomographic position 100.

Figure 13A:
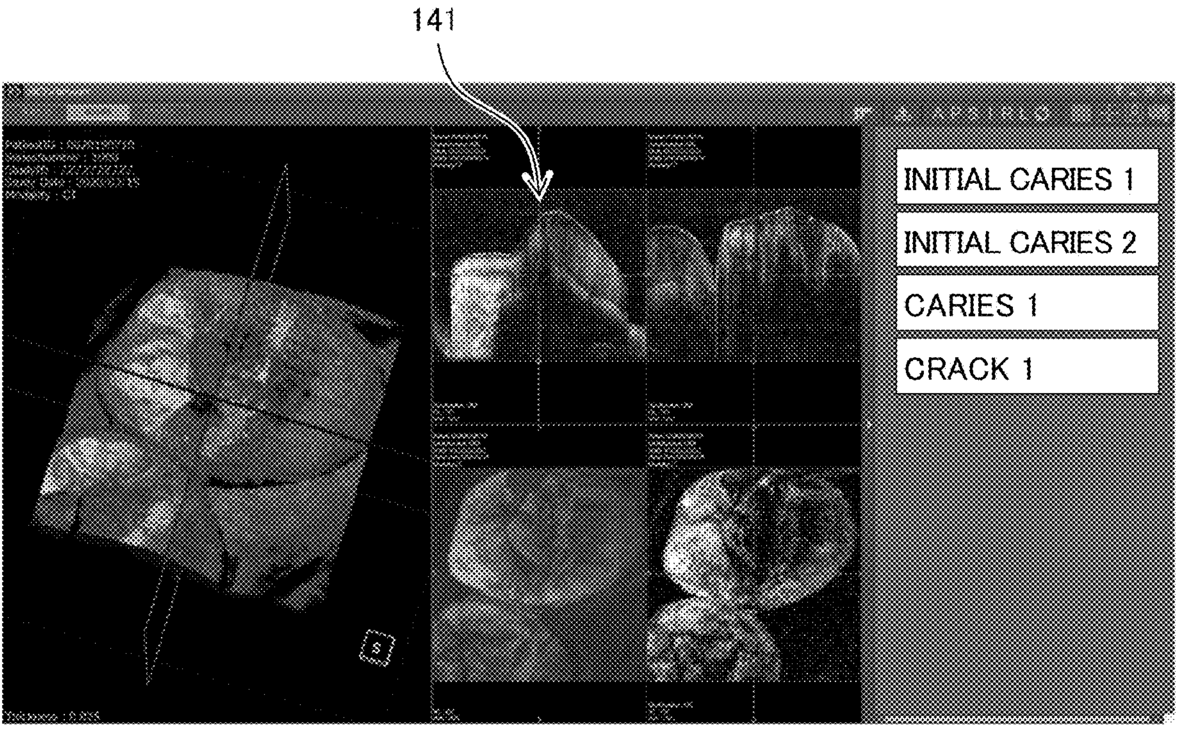
FIG. 13A is a diagram showing a tooth image displayed on the screen before transition.

In the case where the AI image diagnosis apparatus 1 according to Example 1 includes the display controller 12, the OCT 3D image data (diagnostic images) and the detection result 13B (data of representative points of lesion regions) shown in FIG. 12B are inputted to the display controller 12 (OCT 3D viewer). Thereby, the display controller 12 of Example 1 displays the diagnostic images on the display device 15 and also displays the region names as selected information in a list on the display device 15. The displayed region names are determined by the model executor 11 based on the name of the characteristic part (name of lesion) in the lesion information data outputted by the first trained model. FIG. 13A shows an example of the region names and tooth images displayed on the initial screen. In the OCT image viewer, two orthogonal lines indicating the cross-section are displayed respectively on the A-plane tomographic image, L-plane tomographic image, and S-plane tomographic image, and the cross-section is displayed three-dimensionally on the 3D image. Then, by changing the position of the lines indicating the cross-section in the tomographic image, the tomographic image data at the desired tomographic position can be easily extracted. In FIG. 13A, four region names are displayed on the right side of the tooth image.

Figure 13B:
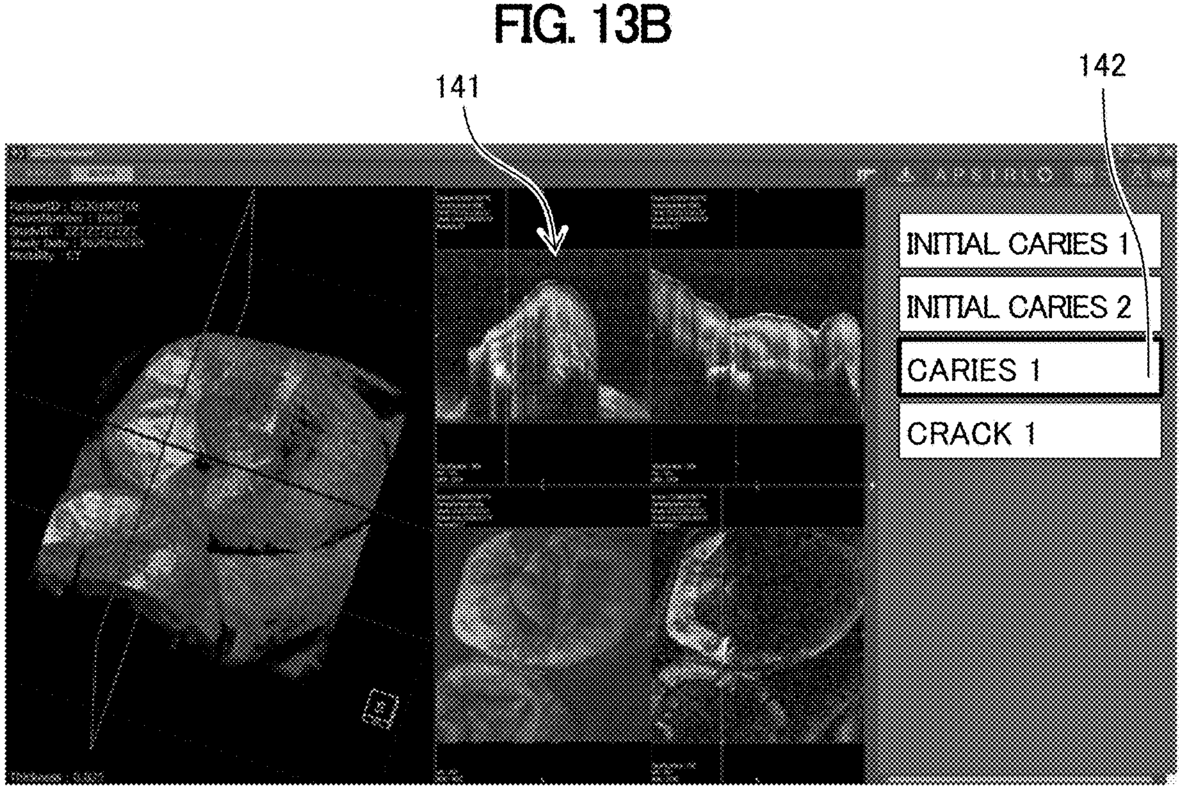
FIG. 13B is a diagram showing a tooth image displayed on the screen after transition.

The user can see this initial screen and perform an operation (click) to select, for example, "caries 1" as the region name (selected information) using the input device 14 such as a mouse. In this case, the display controller 12 of Example 1 searches for the tomographic position and center position of the lesion region (caries 1) associated with that region name from the detection result 13B (data of representative points of lesion regions), and displays the tomographic image with the cross-section moved to the obtained tomographic position and center position as shown in FIG. 13B. FIG. 13B shows the tooth image displayed on the screen after transitioning from the initial screen in FIG. 13A. Reference numeral 141 in FIGS. 13A and 13B indicates the display area of the A-plane tomographic image. The A-plane tomographic image in FIG. 13B is a tomographic image where caries is present, unlike the A-plane tomographic image (initial image) in FIG. 13A. Similarly, in FIG. 13B, tomographic images where caries is present are also displayed in the L-plane tomographic image and S-plane tomographic image.

It can be configured to notify the user of which lesion image is being displayed on the display device 15. In the display screen of FIG. 13B, the frame of the button 142 of the region name (selected information) selected by the user is highlighted with a thick line, but the color of the selected button can be changed.

The present example (Example 1) has been described as inputting OCT 3D images acquired in the measurement imaging mode of the dental OCT device, but instead, it is also possible to input OCT 3D images acquired in the preview imaging mode of the dental OCT device. The dental OCT device described in Patent Literature 1 quickly displays the subject image as a real-time video on the display device in the preview imaging mode. Therefore, for example, the AI image diagnosis apparatus 1 according to Example 1 can acquire the 3D image data being captured in the preview imaging mode (data in the video memory) from the dental OCT device. In this case, the AI image diagnosis apparatus 1 according to Example 1 uses the model executor 11 to input sequentially the tomographic image data constituting the acquired 3D image data being captured to the first trained model. Thereby, the model executor 11 can similarly obtain lesion information data from the first trained model and detect lesions.

Example 2

Next, an example (Example 2) in which the AI image diagnosis apparatus 1 detects lesions in the input OCT 3D images (diagnostic images) using the above-described second trained model will be described. The model executor 11 of the AI image diagnosis apparatus 1 according to Example 2 sequentially inputs the multiple pieces of A-plane tomographic image data in the 3D image data acquired by the dental OCT device to the second trained model in order from front to back (anteroposterior direction). FIG. 9 shows an example of the A-plane tomographic image data sequentially inputted to the second trained model. The model executor 11 of Example 2 can input all the A-plane tomographic image data to the second trained model in order, or can input them to the second trained model every few images. Thereby, Example 2 can process the 3D image data at high speed.

The model executor 11 of the AI image diagnosis apparatus 1 according to Example 2 accepts an instruction of either horizontal scanning or vertical scanning by user operation, for example. At this time, when the model executor 11 accepts the instruction of horizontal scanning, it inputs the A-plane tomographic image data to the second trained model and executes arithmetic processing of the second trained model. Also, when the model executor 11 accepts the instruction of vertical scanning, it inputs the L-plane tomographic image data to the second trained model and executes arithmetic processing of the second trained model.

Alternatively, the model executor 11 can determine the scanning direction based on the input information. In this case, for example, the model executor 11 determines scanning direction information of the dental OCT device when imaging, which is included in the inputted three-dimensional tooth image data. At this time, when the model executor 11 determines that the inputted three-dimensional tooth image data includes horizontal scanning information, it inputs the A-plane tomographic image data to the second trained model and executes arithmetic processing of the second trained model. Also, when the model executor 11 determines that the inputted three-dimensional tooth image data includes vertical scanning information, it inputs the L-plane tomographic image data to the second trained model and executes arithmetic processing of the second trained model.

The second trained model finds lesions from the inputted tomographic image data and outputs lesion information data (name of characteristic part and image representing degree of matching).

The model executor 11 of the AI image diagnosis apparatus 1 according to Example 2 performs analysis with the second trained model on all the tomographic image data, assuming the total number of tomographic positions constituting the diagnostic images is 400, for example. Furthermore, this model executor 11 assigns the degree of similarity to the characteristic part to each point constituting the image in each piece of tomographic image data, and finds lesions such as initial caries, caries, and cracks throughout all the tomographic image data. These names of discovered characteristic parts are used as selected information in the processing of the display controller 12 of the AI image diagnosis apparatus 1 according to Example 2.

Figure 14A:
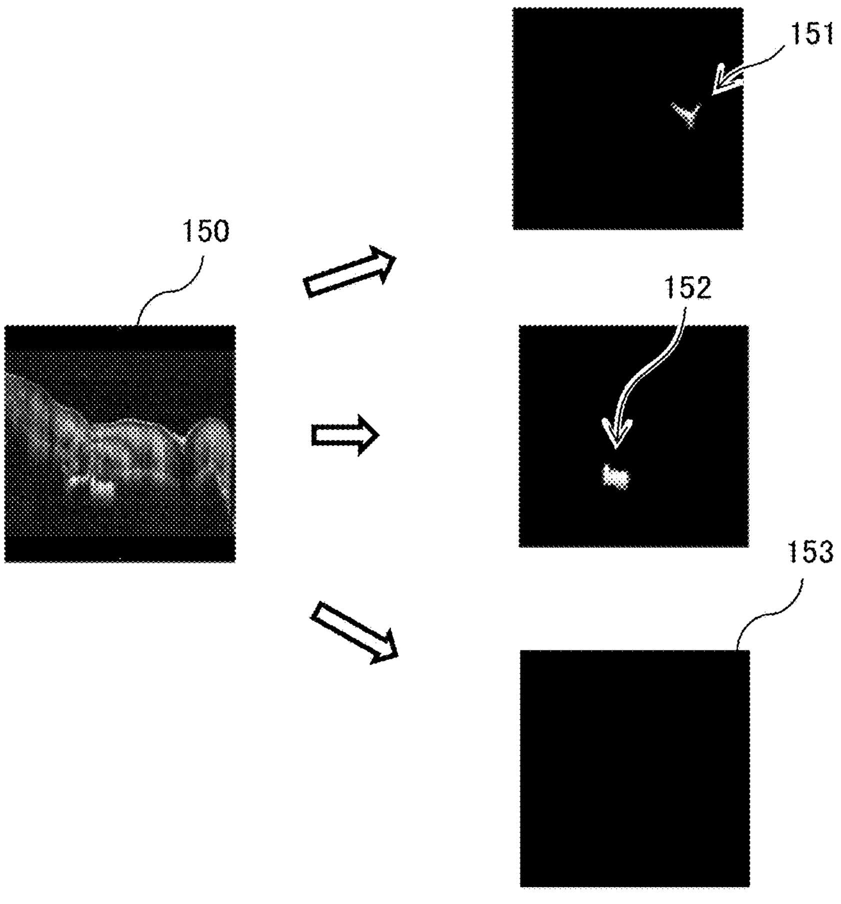
FIG. 14A is a diagram showing input data and three pieces of output data of the second trained model, respectively.

When the tomographic image 150 shown in FIG. 14A is inputted, for example, the second trained model outputs an image representing the degree of matching for each characteristic part. That is, the second trained model outputs three images representing the degree of matching: an image, 151, representing the degree of matching of initial caries, an image, 152, representing the degree of matching of caries, and an image, 153, representing the degree of matching of cracks. In FIG. 14A, the image 153 representing the degree of matching of cracks is just a completely black image because no cracks were found in the tomographic image 150 inputted at this time.

The second trained model performs analysis on all the tomographic image data, and generates as many images representing the degree of matching as the total number of tomographic positions for each name of lesion (name of characteristic part). The model executor 11 of the AI image diagnosis apparatus 1 according to Example 2 obtains the images representing the degree of matching from the second trained model, and reconstructs the images representing the degree of matching for each name of lesion (name of characteristic part) to generate three-dimensional image data. When the model executor 11 reconstructs the images representing the degree of matching of caries for all the tomographic image data, for example, it can generate volume data 154 (see FIG. 14B) of caries only. The three-dimensional image of the characteristic part generated by reconstruction is an example of the detection result 13B (see FIG. 1) of lesions in the input OCT 3D image data (diagnostic images).

Figure 14B:
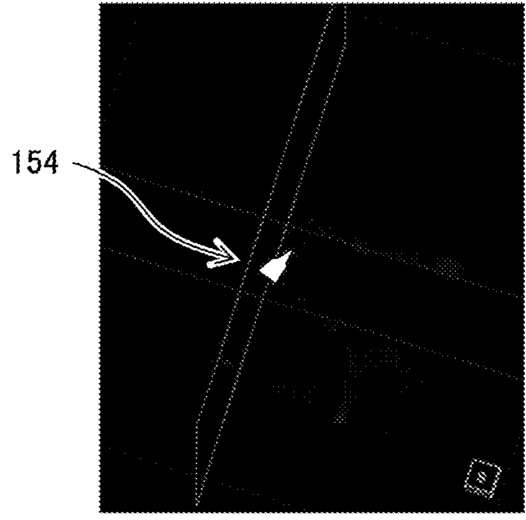
FIG. 14B is a diagram showing reconstructed volume data.
Figure 15A:
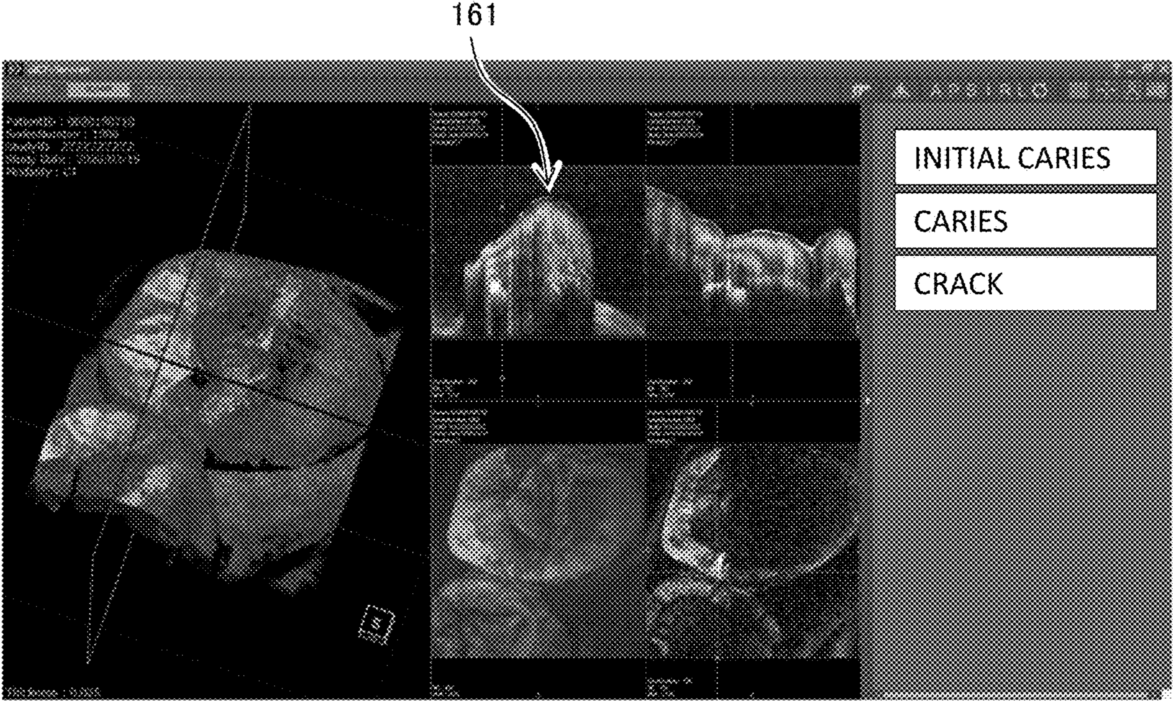
FIG. 15A is a diagram showing a tooth image displayed on the screen.

In the case where the AI image diagnosis apparatus 1 according to Example 2 includes the display controller 12, the OCT 3D image data (diagnostic images) and the volume data (detection result 13B) as shown in FIG. 14B are inputted to the display controller 12 (OCT 3D viewer). Thereby, the display controller 12 of Example 2 displays the diagnostic images on the display device 15 and also displays the names of characteristic parts as selected information in a list on the display device 15. The displayed names of characteristic parts are the names of characteristic parts detected by the second trained model. FIG. 15A shows an example of the names of characteristic parts and tooth images displayed on the initial screen. In FIG. 15A, three names of characteristic parts are displayed on the right side of the tooth image.

Figure 15B:
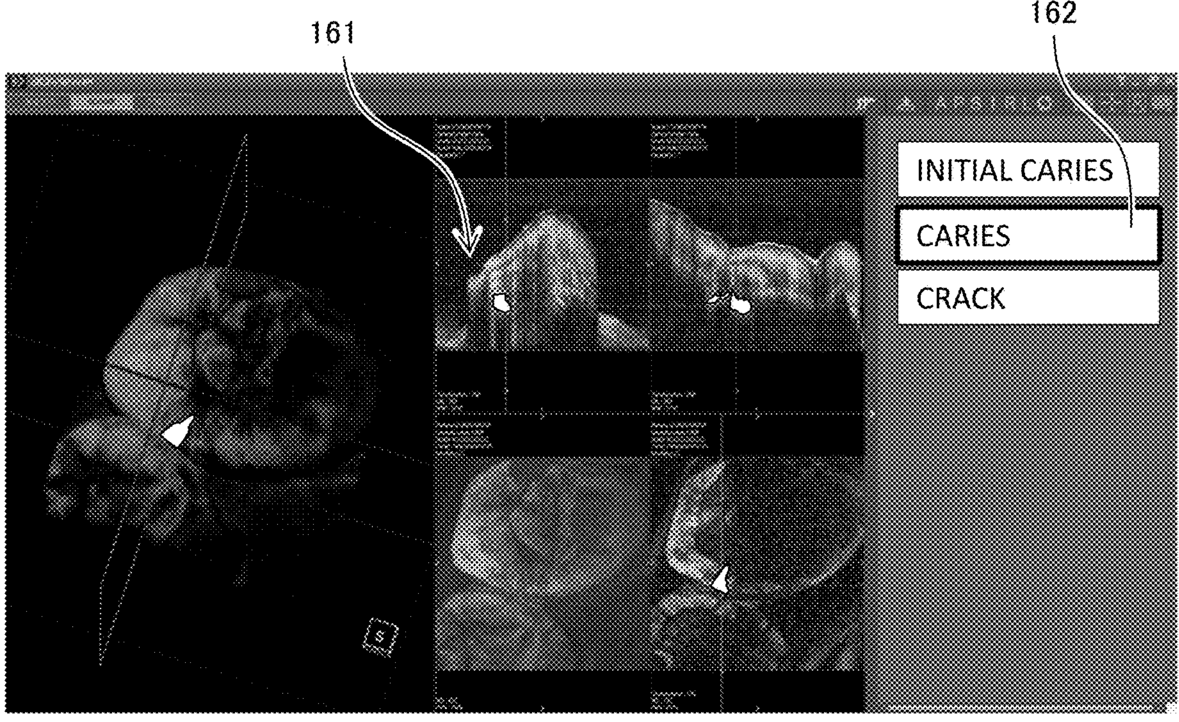
FIG. 15B is a diagram showing a tooth image with volume data superimposed.

The user can see this initial screen and perform an operation (click) to select, for example, "caries" as the name of the characteristic part (selected information) using the input device 14 such as a mouse. In this case, the display controller 12 of Example 2 superimposes the three-dimensional image of the characteristic part (caries) on the OCT 3D image data (diagnostic images) as shown in FIG. 15B to visualize the caries. FIG. 15B shows the tooth image displayed on the screen after transitioning from the initial screen in FIG. 15A. Reference numeral 161 indicates the display area of the A-plane tomographic image. In FIG. 15B, it can be seen that the volume data 154 (see FIG. 14B) of caries only is superimposed on the tooth in the 3D image display area. At this time, the display controller 12 of Example 2 also superimposes the caries-only volume data on the tomographic images. That is, the display controller 12 superimposes and displays the image representing the degree of matching on each of the A-plane tomographic image, L-plane tomographic image, and S-plane tomographic image.

In the example shown in FIG. 15B, one characteristic part is displayed on one screen, but multiple characteristic parts can be displayed on one screen, or each characteristic part can be color-coded. It can be configured to notify the user of what lesion the three-dimensional image of the characteristic part being displayed on the display device 15 is. In the screen of FIG. 15B, the frame of the button 162 of the name of the characteristic part (selected information) selected by the user is highlighted with a thick line, but the color of the selected button can be changed for display.

According to Example 2, by superimposing the three-dimensional image of the lesion characteristic part on the OCT 3D image data, the position and extent of the lesion can be grasped more easily visually and quantitatively (area, volume).

Also, in the case where the second trained model is constructed by inputting dental plaque as a name other than a lesion in the label added to the training data in the training stage, Example 2 can superimpose the three-dimensional image of the plaque characteristic part on the OCT 3D image data of the tooth. Generally, in tooth brushing instruction, after the patient brushes their teeth, the plaque is stained with a plaque staining agent, and the patient checks the areas they missed and receives instruction. If the staining agent adheres to clothing, the color becomes difficult to remove, so that caution is required. In contrast, according to Example 2, the plaque adhesion state can be visualized and grasped quantitatively, so that it can be used for tooth brushing instruction without using a staining agent.

[Hardware Configuration]

Figure 16:
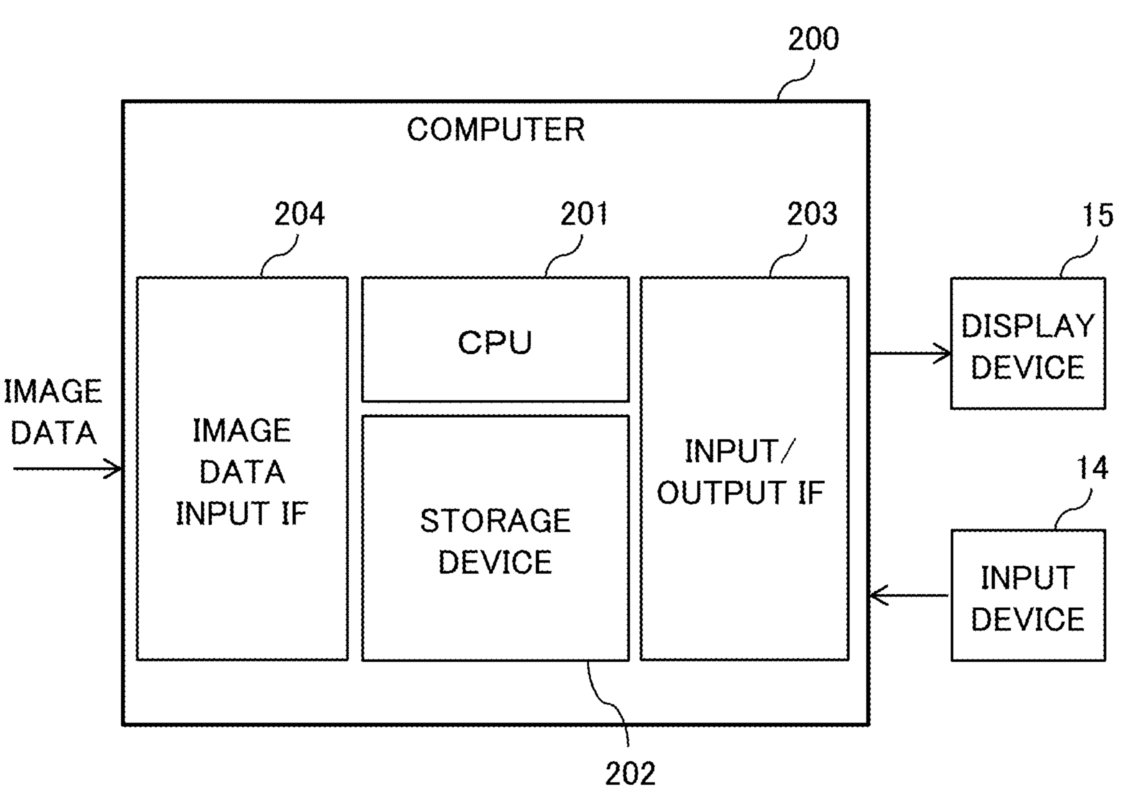
FIG. 16 is a hardware configuration diagram showing an example of a computer that carries out the functions of the AI image diagnosis apparatus according to an embodiment of the present invention.

Next, an example of the hardware configuration of a computer that carries out the functions of the AI image diagnosis apparatus 1 according to the present embodiment will be described with reference to FIG. 16. The computer 200 has a CPU 201, a storage device 202, an input/output IF (interface) 203, and an image data input IF 204.

The CPU 201 operates based on a program stored in the storage device 202 and performs control by the controller (model executor 11, display controller 12 shown in FIG. 1). The CPU 201 controls the input device 14 such as a mouse or keyboard and the display device 15 such as a liquid crystal display via the input/output IF 203. The CPU 201 acquires data from the input device 14 via the input/output IF 203 and also outputs generated data to the display device 15. A GPU (Graphics Processing Unit) or the like may be used in addition to the CPU 201 as a processor.

The storage device 202 is equipped with a ROM, RAM, HDD, etc. The storage device 202 stores a boot program executed by the CPU 201 at startup of the computer 200, programs related to the hardware of the computer 200, etc. The storage device 202 stores programs (trained model execution program, viewer program) executed by the CPU 201 and data used by those programs, etc.

The image data input IF 204 is equipped with a communication IF, media IF, etc. The image data input IF 204 receives image data from other devices via a communication network and outputs it to the CPU 201, or reads image data stored in a recording medium and outputs it to the CPU 201 via the storage device 202. For example, when the computer 200 functions as the AI image diagnosis apparatus 1 according to the embodiment, the CPU 201 carries out the functions of the AI image diagnosis apparatus 1 by executing the trained model execution program and viewer program loaded on the RAM.

[Dental OCT Image Diagnosis Apparatus]

Figure 17:
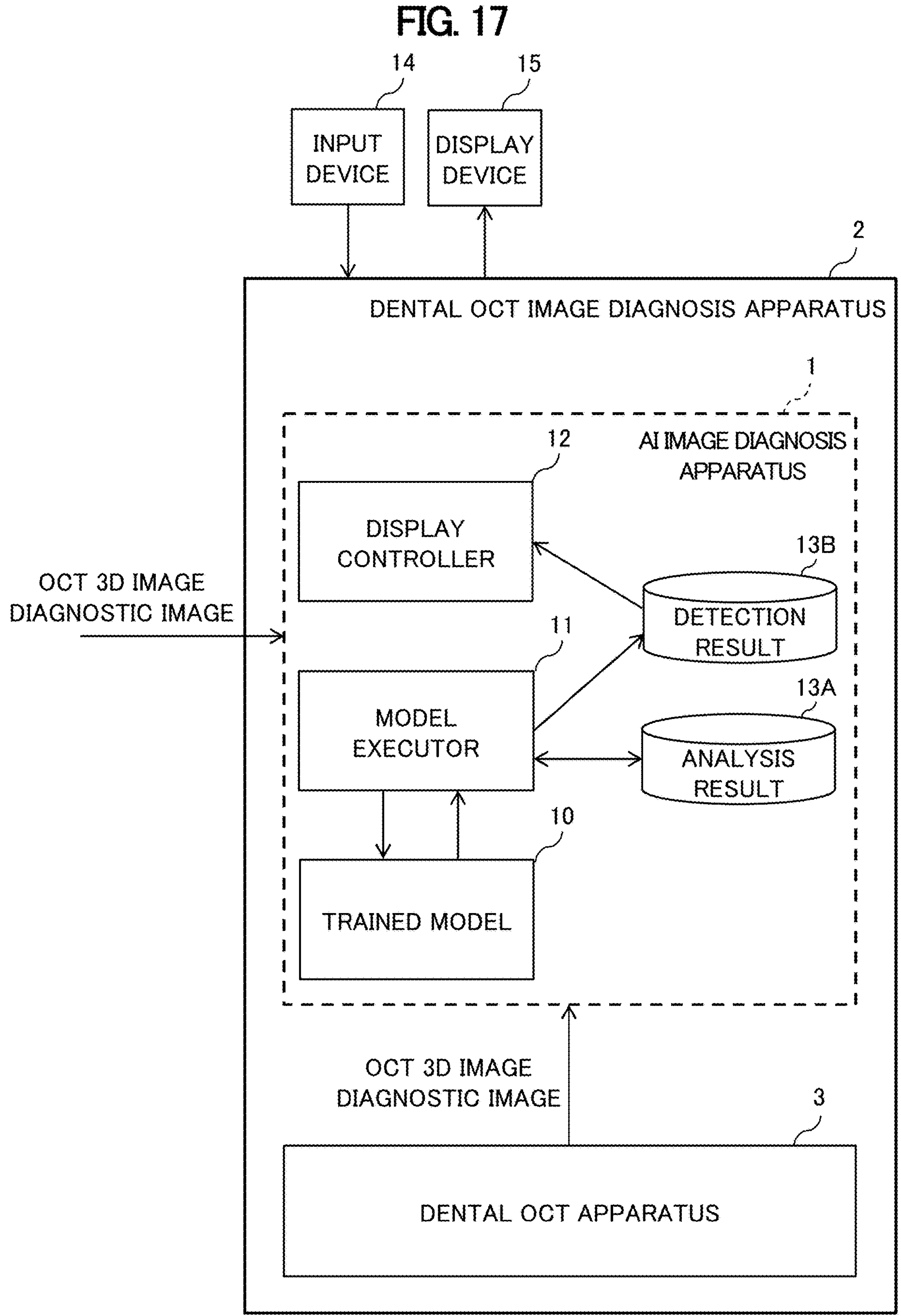
FIG. 17 is a functional block diagram of the dental OCT image diagnosis apparatus according to an embodiment of the present invention.

Next, the dental OCT image diagnosis apparatus according to an embodiment of the present invention will be described with reference to FIG. 17. The dental OCT image diagnosis apparatus 2 is configured by installing the AI image diagnosis apparatus 1 in the dental OCT device 3. The AI image diagnosis apparatus 1 has already been described, so that its description is omitted. The dental OCT device 3 is equipped with various configurations necessary for imaging tooth images. The dental OCT device 3 is equipped with, for example, an OCT light source, respective optical systems for measurement light and reference light branched from the laser light emitted from the OCT light source. The dental OCT device 3 is further equipped with a two-dimensional scanning mechanism for scanning the measurement light, a detector for detecting light combined from the reflected light from the tooth and the reference light, a controller, etc. Such a configuration is conventionally known, and the OCT device described in Patent Literature 1 or Patent Literature 2, for example, can be adopted as the dental OCT device 3. The dental OCT image diagnosis apparatus 2 enables consistent operations from imaging to image diagnosis.

The AI image diagnosis apparatus and dental OCT image diagnosis apparatus according to an embodiment of the present invention have been described above, but the gist of the present invention is not limited to these descriptions and should be broadly interpreted based on the description of the claims. It goes without saying that those based on these descriptions, with various modifications, alterations, etc., are also included in the gist of the present invention. For example, the AI image diagnosis apparatus 1 shown in FIGS. 1 and 17 is configured to include the display controller 12 and the display device 15, but neither is an essential configuration. When a viewer is provided separately from the AI image diagnosis apparatus, that viewer can display the OCT 3D images (diagnostic images) inputted to the AI image diagnosis apparatus and the lesion detection result, etc., detected by the AI image diagnosis apparatus.

REFERENCE SIGNS LIST

1 AI image diagnosis apparatus
2 Dental OCT image diagnosis apparatus
3 Dental OCT device
10 Trained model
11 Model executor
12 Display controller
13A Analysis result
13B Detection result
14 Input device
15 Display device
20 Computer
21 CPU
22 Storage device
24 Input device
25 Display device
30 Training data
40 Model constructor
41 CPU
42 Storage device
43 Model construction processing program

The invention claimed is:

1. An AI image diagnosis apparatus into which three-dimensional tooth image data captured by a dental Optical Coherence Tomography (OCT) device is input and which analyzes the input three-dimensional tooth image data, the apparatus comprising:

a processor configured to execute functions of:

a model executor that sequentially inputs two-dimensional tomographic image data constituting the diagnostic target three-dimensional tooth image data into a trained model to output, for each tomographic image, lesion information including at least an image representing per-pixel degree of matching to a lesion class and that reconstructs a three-dimensional volume based on images representing per-pixel degrees of matching; and a display controller that superimposes the reconstructed three-dimensional volume on the input three-dimensional tooth image data for display, wherein lesions are detected in the three-dimensional tooth image data based on the lesion information, wherein the trained model is constructed by machine learning using training data, and wherein training data includes at least one of A-plane tomographic image data which is parallel to a plane specified by both a B-axis direction orthogonal to the A-axis direction, which is an irradiation direction of OCT laser light on the tooth, and the A-axis direction, L-plane tomographic image data which is parallel to a plane specified by both a V-axis direction, orthogonal to the A-axis direction and the B-axis direction, and the A-axis direction, S-plane tomographic image data which is parallel to a plane specified by both the B-axis direction and the V-axis direction, en-face image data synthesized from information on a surface of the tooth irradiated with the OCT laser light and information on the A-axis direction, and three-dimensional image data composed of several consecutive pieces of tomographic image data.

2. The AI image diagnosis apparatus according to claim 1, wherein pixels with a degree of matching less than a predetermined threshold are converted to zero before the reconstructing.

3. The AI image diagnosis apparatus according to claim 2, wherein the predetermined threshold is adaptively determined based on statistics of the degrees of matching across tomographic positions for each lesion class within the input three-dimensional tooth image data.

4. The AI image diagnosis apparatus according to claim 1, wherein the two-dimensional tomographic image data sequentially inputted to the trained model by the model executor is the tomographic image data constituting the three-dimensional tooth image data being captured by the dental OCT device.

5. The AI image diagnosis apparatus according to claim 1, wherein the model executor reconstructs class-specific three-dimensional detection volumes from the images representing per-pixel degrees of matching, and the display controller superimposes a selected class-specific volume on the input three-dimensional tooth image data.

6. The AI image diagnosis apparatus according to claim 1, wherein the display controller lists detected items as selectable entries and, upon user selection, highlights lesion boundaries with a color-coded overlay while displaying corresponding tomographic images.

7. The AI image diagnosis apparatus according to claim 1, wherein the training data further includes tomographic images containing lesion characteristic parts and tomographic images containing non-lesion characteristic parts captured by a dental OCT device.

8. The AI image diagnosis apparatus according to claim 7, wherein the training data further includes labels indicating at least a lesion label and a tooth type.

9. An AI image diagnosis apparatus into which three-dimensional tooth image data captured by a dental Optical Coherence Tomography (OCT) device is input and which analyzes the input three-dimensional tooth image data, the apparatus comprising:

a processor configured to execute functions of:

a model executor that sequentially inputs two-dimensional tomographic image data into a trained model to obtain, for each tomographic image, lesion information including at least a lesion class name, a center position of a point having the highest degree of similarity, and a degree of similarity and that graphs, for each lesion class, a relationship between tomographic positions and degrees of similarity based on the lesion information, identifies, continuous regions in which the degree of similarity exceeds a predetermined threshold over consecutive tomographic positions, determines, a region name for each identified region, associates, the lesion class name, a tomographic position of the highest degree of similarity within the region, and the corresponding center position with the region name to generate a lesion detection result, and that reconstructs a three-dimensional similarity volume from images representing per-pixel degrees of matching output from the trained model; and a display controller that superimposes the reconstructed volume on the input three-dimensional tooth image data for display, and, upon user selection of the region name, extracts and displays tomographic image data corresponding to the selected region, wherein the trained model is constructed by machine learning using training data, and wherein the training data includes at least one of A-plane tomographic image data which is parallel to a plane specified by both a B-axis direction orthogonal to the A-axis direction, which is an irradiation direction of OCT laser light on the tooth, and the A-axis direction, L-plane tomographic image data which is parallel to a plane specified by both a V-axis direction, orthogonal to the A-axis direction and the B-axis direction, and the A-axis direction, S-plane tomographic image data which is parallel to a plane specified by both the B-axis direction and the V-axis direction, en-face image data synthesized from information on a surface of the tooth irradiated with the OCT laser light and information on the A-axis direction, and three-dimensional image data composed of several consecutive pieces of tomographic image data.

10. The AI image diagnosis apparatus according to claim 9, wherein pixels with a degree of similarity less than the predetermined threshold are converted to zero prior to the reconstructing.

11. The AI image diagnosis apparatus according to claim 10, wherein the predetermined threshold is adaptively determined based on statistics of the degrees of similarity across tomographic positions for each lesion class within the input three-dimensional tooth image data.

12. The AI image diagnosis apparatus according to claim 9, wherein the model executor accepts an instruction of either horizontal scanning or vertical scanning by user operation, and upon acceptance of the instruction of horizontal scanning, inputs the A-plane tomographic image data to the trained model, and upon acceptance of the instruction of vertical scanning, inputs the L-plane tomographic image data to the trained model, and executes arithmetic processing of the trained model.

13. The AI image diagnosis apparatus according to claim 9, wherein the model executor determines scanning direction information of the dental OCT device when imaging, which is included in the inputted three-dimensional tooth image data, and upon determination that the inputted three-dimensional tooth image data includes horizontal scanning information, inputs the A-plane tomographic image data to the trained model, and upon determination that the inputted three-dimensional tooth image data includes vertical scanning.

14. A dental OCT image diagnosis apparatus comprising: the AI image diagnosis apparatus according to claim 9 installed in a dental OCT device.

* * * * *